US008252538B2

(12) United States Patent
Croce et al.

(10) Patent No.: US 8,252,538 B2
(45) Date of Patent: Aug. 28, 2012

(54) MICRORNA EXPRESSION SIGNATURE FOR PREDICTING SURVIVAL AND METASTASES IN HEPATOCELLULAR CARCINOMA

(75) Inventors: Carlo M. Croce, Columbus, OH (US); Xin W. Wang, Rockville, MD (US); Anuradha Budhu, College Park, MD (US); Zhao-you Tang, Shanghai (CN)

(73) Assignees: The Ohio State University, Columbus, OH (US); The United States of America as represented by the Secretary of the Department of Health and Human Services National Institute of Health, Office of Technology Transfer, Washington, DC (US); Liver Cancer Institute and Zhongshan Hospital, Fudan University, Shangai (CN)

(*) Notice: Subject to any disclaimer, the term of this patent is extended or adjusted under 35 U.S.C. 154(b) by 404 days.

(21) Appl. No.: 12/513,219

(22) PCT Filed: Nov. 1, 2007

(86) PCT No.: PCT/US2007/023660
§ 371 (c)(1),
(2), (4) Date: Nov. 16, 2009

(87) PCT Pub. No.: WO2008/054828
PCT Pub. Date: May 8, 2008

(65) Prior Publication Data
US 2010/0120898 A1 May 13, 2010

Related U.S. Application Data

(60) Provisional application No. 60/855,895, filed on Nov. 1, 2006.

(51) Int. Cl.
*C12Q 1/68* (2006.01)
*C07H 21/02* (2006.01)
*C07H 21/04* (2006.01)

(52) U.S. Cl. ...... 435/6.11; 435/6.1; 435/6.14; 536/23.1; 536/24.3

(58) Field of Classification Search ............... None
See application file for complete search history.

(56) References Cited

U.S. PATENT DOCUMENTS

| | | |
|---|---|---|
| 4,172,124 A | 10/1979 | Koprowski et al. |
| 4,196,265 A | 4/1980 | Koprowski et al. |
| 4,608,337 A | 8/1986 | Croce |
| 4,693,975 A | 9/1987 | Kozbor et al. |
| 4,701,409 A | 10/1987 | Croce |
| 5,015,568 A | 5/1991 | Tsujimoto et al. |
| 5,149,628 A | 9/1992 | Croce |
| 5,198,338 A | 3/1993 | Croce |
| 5,202,429 A | 4/1993 | Tsujimoto et al. |
| 5,459,251 A | 10/1995 | Tsujimoto et al. |
| 5,506,106 A | 4/1996 | Croce et al. |
| 5,506,344 A | 4/1996 | Tsujimoto et al. |
| 5,523,393 A | 6/1996 | Tsujimoto et al. |
| 5,567,586 A | 10/1996 | Croce |
| 5,595,869 A | 1/1997 | Tsujimoto et al. |
| 5,633,135 A | 5/1997 | Croce et al. |
| 5,633,136 A | 5/1997 | Croce et al. |
| 5,674,682 A | 10/1997 | Croce et al. |
| 5,688,649 A | 11/1997 | Croce et al. |
| 5,695,944 A | 12/1997 | Croce et al. |
| 5,928,884 A | 7/1999 | Croce et al. |
| 5,939,258 A | 8/1999 | Croce et al. |
| 5,985,598 A | 11/1999 | Russo et al. |
| 6,040,140 A | 3/2000 | Croce et al. |
| 6,130,201 A | 10/2000 | Croce et al. |
| 6,187,536 B1 | 2/2001 | Weinberg et al. |
| 6,242,212 B1 | 6/2001 | Croce et al. |
| 6,255,293 B1 | 7/2001 | Kimchi |
| 6,258,541 B1 | 7/2001 | Chapkin et al. |
| 6,774,217 B1 | 8/2004 | Croce et al. |
| 6,924,414 B2 | 8/2005 | Croce et al. |
| 7,060,811 B2 | 6/2006 | Aldaz et al. |
| 7,141,417 B1 | 11/2006 | Croce et al. |
| 7,175,995 B1 | 2/2007 | Russo et al. |
| 7,217,568 B2 | 5/2007 | Jamieson et al. |
| 7,220,834 B2 | 5/2007 | Croce et al. |
| 7,232,806 B2 | 6/2007 | Tuschl et al. |
| 7,390,792 B2 | 6/2008 | Srivastava et al. |
| 7,585,969 B2 | 9/2009 | Stoffel et al. |
| 7,592,441 B2 | 9/2009 | Bentwich et al. |
| 7,618,814 B2 | 11/2009 | Bentwich et al. |
| 7,642,348 B2 | 1/2010 | Bentwich et al. |
| 7,667,090 B2 | 2/2010 | Croce |

(Continued)

FOREIGN PATENT DOCUMENTS

CA 2587189 12/2006

(Continued)

OTHER PUBLICATIONS

Lui et al Cancer Research. 2007. 67: 6031.*
Liu et al . Clinical Immunology. 2004. 112: 225-230.*
Coleman et al. Drug Discovery Today. 2003. 8: 233-235.*
Saetre et al. Molecular Brain Research. 2004. 126: 198-206.*
Palmer et al. BMC Genomics. 2006. 7:115.*
Lu et al. Nature. Jun. 2005. 435. 834-838.*
European Communication Pursuant to Article 94(3) EPC, Application No. 07867402.5, dated Jan. 5, 2011.
European Search Report, Application No. 08799295.4-2402, PCT/US2008/075565, dated Nov. 9, 2010.

(Continued)

*Primary Examiner* — Carla Myers
(74) *Attorney, Agent, or Firm* — MacMillan, Sobanski & Todd, LLC

(57) ABSTRACT

Provided herein are methods and compositions for the diagnosis, prognosis and treatment of Hepatocellular carcinoma (HCC). Also provided are methods of identifying anti-HCC agents.

9 Claims, 12 Drawing Sheets
(4 of 12 Drawing Sheet(s) Filed in Color)

U.S. PATENT DOCUMENTS

| | | |
|---|---|---|
| 7,670,840 B2 | 3/2010 | Croce et al. |
| 7,709,616 B2 | 5/2010 | Bentwich et al. |
| 7,723,030 B2 | 5/2010 | Croce et al. |
| 7,723,035 B2 | 5/2010 | Croce et al. |
| 7,728,189 B2 | 6/2010 | Croce |
| 7,749,715 B2 | 7/2010 | Russo et al. |
| 7,777,005 B2 | 8/2010 | Croce et al. |
| 2001/0026796 A1 | 10/2001 | Croce et al. |
| 2002/0086331 A1 | 7/2002 | Croce et al. |
| 2002/0116726 A1 | 8/2002 | Croce et al. |
| 2002/0132290 A1 | 9/2002 | Frazer |
| 2004/0033502 A1 | 2/2004 | Williams et al. |
| 2004/0078834 A1 | 4/2004 | Croce |
| 2004/0152112 A1 | 8/2004 | Croce et al. |
| 2004/0265316 A1 | 12/2004 | Croce et al. |
| 2004/0265930 A1 | 12/2004 | Sun et al. |
| 2005/0019890 A1 | 1/2005 | Croce |
| 2005/0059005 A1 | 3/2005 | Tuschl et al. |
| 2005/0069918 A1 | 3/2005 | Claret |
| 2005/0074797 A1 | 4/2005 | Croce et al. |
| 2005/0075492 A1 | 4/2005 | Chen et al. |
| 2005/0112630 A1 | 5/2005 | Shaughnessy et al. |
| 2005/0164252 A1 | 7/2005 | Yeung |
| 2005/0176025 A1 | 8/2005 | McSwiggen et al. |
| 2005/0181385 A1 | 8/2005 | Linsley et al. |
| 2005/0186589 A1 | 8/2005 | Kowalik et al. |
| 2005/0256072 A1 | 11/2005 | Aronin et al. |
| 2005/0260639 A1 | 11/2005 | Nakamura et al. |
| 2005/0266443 A1 | 12/2005 | Croce et al. |
| 2005/0287530 A1 | 12/2005 | Croce et al. |
| 2006/0019286 A1 | 1/2006 | Horvitz et al. |
| 2006/0024780 A1 | 2/2006 | Aldaz et al. |
| 2006/0037088 A1 | 2/2006 | Li |
| 2006/0075511 A1 | 4/2006 | Croce et al. |
| 2006/0084059 A1 | 4/2006 | Yip et al. |
| 2006/0099619 A1 | 5/2006 | Remacle et al. |
| 2006/0105340 A1 | 5/2006 | Croce et al. |
| 2006/0105360 A1 | 5/2006 | Croce et al. |
| 2006/0127895 A1 | 6/2006 | Sabapathy |
| 2006/0165659 A1 | 7/2006 | Croce et al. |
| 2006/0166918 A1 | 7/2006 | Heidenreich et al. |
| 2006/0185027 A1 | 8/2006 | Bartel et al. |
| 2006/0188924 A1 | 8/2006 | Russo et al. |
| 2006/0188959 A1 | 8/2006 | Croce et al. |
| 2006/0189557 A1 | 8/2006 | Slack et al. |
| 2006/0247448 A1 | 11/2006 | Boivin et al. |
| 2006/0292616 A1 | 12/2006 | Neely et al. |
| 2007/0036765 A1 | 2/2007 | Civin et al. |
| 2007/0050146 A1 | 3/2007 | Bentwich et al. |
| 2007/0054849 A1 | 3/2007 | Nakamura et al. |
| 2007/0065840 A1 | 3/2007 | Naguibneva et al. |
| 2007/0065844 A1 | 3/2007 | Golub et al. |
| 2007/0072230 A1 | 3/2007 | Croce et al. |
| 2007/0099196 A1 | 5/2007 | Kauppinen et al. |
| 2007/0123482 A1 | 5/2007 | Stoffel et al. |
| 2007/0161004 A1 | 7/2007 | Brown et al. |
| 2007/0178105 A1 | 8/2007 | Croce et al. |
| 2007/0178502 A1 | 8/2007 | Reed |
| 2007/0212727 A1 | 9/2007 | Szalay et al. |
| 2007/0213292 A1 | 9/2007 | Stoffel et al. |
| 2007/0259352 A1 | 11/2007 | Bentwich et al. |
| 2007/0292878 A1 | 12/2007 | Raymond |
| 2008/0026951 A1 | 1/2008 | Brown et al. |
| 2008/0050744 A1 | 2/2008 | Brown et al. |
| 2008/0166707 A1 * | 7/2008 | Han .................. 435/6 |
| 2008/0171667 A1 | 7/2008 | Brown et al. |
| 2008/0176766 A1 | 7/2008 | Brown et al. |
| 2008/0182245 A1 | 7/2008 | Brown et al. |
| 2008/0193943 A1 | 8/2008 | Murray |
| 2008/0254473 A1 | 10/2008 | Chen et al. |
| 2008/0256650 A1 | 10/2008 | Croce |
| 2008/0261908 A1 | 10/2008 | Croce et al. |
| 2008/0306006 A1 | 12/2008 | Croce et al. |
| 2008/0306017 A1 | 12/2008 | Croce et al. |
| 2008/0306018 A1 | 12/2008 | Croce et al. |
| 2009/0005336 A1 | 1/2009 | Wang |
| 2009/0023594 A1 | 1/2009 | Mouritzen et al. |
| 2009/0029932 A1 | 1/2009 | Voinnet et al. |
| 2009/0061424 A1 | 3/2009 | Chen |
| 2009/0092974 A1 | 4/2009 | Davison et al. |
| 2009/0099034 A1 | 4/2009 | Ahlquist et al. |
| 2009/0123533 A1 | 5/2009 | Croce et al. |
| 2009/0123912 A1 | 5/2009 | Raymond |
| 2009/0123933 A1 | 5/2009 | Mishra |
| 2009/0131348 A1 | 5/2009 | Labourier et al. |
| 2009/0131354 A1 | 5/2009 | Bader et al. |
| 2009/0131356 A1 | 5/2009 | Bader et al. |
| 2009/0163430 A1 | 6/2009 | Johnson et al. |
| 2009/0163434 A1 | 6/2009 | Bader et al. |
| 2009/0163435 A1 | 6/2009 | Bader et al. |
| 2009/0175827 A1 | 7/2009 | Byrom et al. |
| 2009/0176723 A1 | 7/2009 | Brown et al. |
| 2009/0192102 A1 | 7/2009 | Bader et al. |
| 2009/0192111 A1 | 7/2009 | Bader et al. |
| 2009/0192114 A1 | 7/2009 | Ovcharenko et al. |
| 2009/0209450 A1 | 8/2009 | Croce et al. |
| 2009/0222934 A1 | 9/2009 | Croce |
| 2009/0227533 A1 | 9/2009 | Bader et al. |
| 2009/0232893 A1 | 9/2009 | Bader et al. |
| 2009/0233297 A1 | 9/2009 | Mambo et al. |
| 2009/0253780 A1 | 10/2009 | Takeshita et al. |
| 2009/0263803 A1 | 10/2009 | Beaudenon et al. |
| 2009/0270484 A1 | 10/2009 | Croce et al. |
| 2009/0281167 A1 | 11/2009 | Shen et al. |
| 2009/0306194 A1 | 12/2009 | Ford et al. |
| 2010/0004322 A1 | 1/2010 | Croce |
| 2010/0048681 A1 | 2/2010 | Croce |
| 2010/0120898 A1 | 5/2010 | Croce et al. |
| 2010/0137410 A1 | 6/2010 | Croce |
| 2010/0144850 A1 | 6/2010 | Croce |
| 2010/0173319 A1 | 7/2010 | Croce et al. |
| 2010/0184032 A1 | 7/2010 | Georgantas et al. |
| 2010/0184830 A1 | 7/2010 | Croce et al. |
| 2010/0184842 A1 | 7/2010 | Croce |
| 2010/0192235 A1 | 7/2010 | Croce |
| 2010/0197770 A1 | 8/2010 | Wang et al. |
| 2010/0197774 A1 | 8/2010 | Croce et al. |
| 2010/0203544 A1 | 8/2010 | Croce et al. |
| 2010/0234241 A1 | 9/2010 | Croce et al. |
| 2010/0249213 A1 | 9/2010 | Croce |
| 2010/0257618 A1 | 10/2010 | Croce et al. |
| 2010/0317610 A1 | 12/2010 | Croce |
| 2011/0015080 A1 * | 1/2011 | Golub et al. .................. 506/2 |

FOREIGN PATENT DOCUMENTS

| | | |
|---|---|---|
| FR | 2877350 | 5/2006 |
| WO | 90/15156 | 12/1990 |
| WO | 91/00364 | 1/1991 |
| WO | 91/07424 | 5/1991 |
| WO | 93/12136 | 6/1993 |
| WO | 94/10343 | 5/1994 |
| WO | 94/24308 | 10/1994 |
| WO | 94/26930 | 11/1994 |
| WO | 96/13514 | 5/1996 |
| WO | 96/35124 | 11/1996 |
| WO | 97/29119 | 8/1997 |
| WO | 98/09510 | 3/1998 |
| WO | 00/03685 | 1/2000 |
| WO | 00/50565 | 8/2000 |
| WO | 00/55169 | 9/2000 |
| WO | 0076524 | 12/2000 |
| WO | 01/44466 | 6/2001 |
| WO | 01/68666 | 9/2001 |
| WO | 01/77343 | 10/2001 |
| WO | 01/87958 | 11/2001 |
| WO | 02/064171 | 8/2002 |
| WO | 02/064172 | 8/2002 |
| WO | 03/029459 | 4/2003 |
| WO | 03/029459 A2 | 4/2003 |
| WO | 03/078662 | 9/2003 |
| WO | 03/092370 | 11/2003 |
| WO | 2004/033659 | 4/2004 |
| WO | 2004/043387 | 5/2004 |
| WO | 2004/079013 | 9/2004 |
| WO | 2004/098377 | 11/2004 |
| WO | 2005/017711 | 2/2005 |
| WO | 2005/020795 | 3/2005 |

| | | |
|---|---|---|
| WO | 2005060661 | 7/2005 |
| WO | 2005/078139 | 8/2005 |
| WO | 2005/078139 A2 | 8/2005 |
| WO | 2005/080601 | 9/2005 |
| WO | 2005/118806 | 12/2005 |
| WO | 2006/105486 | 10/2006 |
| WO | 2006/108718 | 10/2006 |
| WO | 2006108718 | 10/2006 |
| WO | 2006/119266 | 11/2006 |
| WO | 2006/133022 | 12/2006 |
| WO | 2006/137941 | 12/2006 |
| WO | 2007/016548 | 2/2007 |
| WO | 2007/033023 | 3/2007 |
| WO | 2007/044413 | 4/2007 |
| WO | 2007/081680 | 7/2007 |
| WO | 2007/081720 | 7/2007 |
| WO | 2007/081740 | 7/2007 |
| WO | 2007/084486 | 7/2007 |
| WO | 2007/109236 | 9/2007 |
| WO | 2007112097 | 10/2007 |
| WO | 2007/127190 | 11/2007 |
| WO | 2008/008430 | 1/2008 |
| WO | 2008/036776 | 3/2008 |
| WO | 2008/054828 | 5/2008 |
| WO | 2008/054828 C | 5/2008 |
| WO | 2008/070082 | 6/2008 |
| WO | 2008/073920 | 6/2008 |
| WO | 2008073915 | 6/2008 |
| WO | 2008/094545 | 8/2008 |
| WO | 2008/097277 | 8/2008 |
| WO | 2008/136971 | 11/2008 |
| WO | 2008/153987 | 12/2008 |
| WO | 2008/157319 | 12/2008 |
| WO | 2009/018303 | 2/2009 |
| WO | 2009/020905 | 2/2009 |
| WO | 2009/026487 | 2/2009 |
| WO | 2009/033140 | 3/2009 |
| WO | 2009/049129 | 4/2009 |
| WO | 2009/055773 | 4/2009 |
| WO | 2009/064590 | 5/2009 |
| WO | 2009/070653 | 6/2009 |
| WO | 2009/100029 | 8/2009 |
| WO | 2009/108853 | 9/2009 |
| WO | 2009/108856 | 9/2009 |
| WO | 2009/108860 | 9/2009 |
| WO | 2009/108866 | 9/2009 |
| WO | 2009/152300 | 12/2009 |
| WO | 2010/019694 | 2/2010 |
| WO | 2010/059779 | 5/2010 |
| WO | 2010/065156 | 6/2010 |
| WO | 2010/099161 | 9/2010 |

OTHER PUBLICATIONS

European Search Report, Application No. 08798444.9-2402, PCT/US2008/073964, dated Dec. 16, 2010.
European Seach Report, Application No. 11151749.6, dated Feb. 8, 2011.
PCT Internatioanl Preliminary Report on Patentability, PCT/US2009/038214 filed Mar. 25, 2009, dated Jun. 16, 2011.
European Supplementary Search Report, Application No. 09715064.3 dated May 24, 2011.
Canadian Office Action, Application No. 2,617,581, dated Feb. 1, 2011.
European Search Reoprt, Application No. 08841700.1, dated Jan. 4, 2011.
European Communication Pursuant to Article 94(3) EPC, Application No. 08768266.2, dated Apr. 18, 2011.
PCT International Preliminary Report on Patentability, PCT/US2009/065072 filed Nov. 19, 2009, dated Jun. 3, 2011.
European Communication Pursuant to Article 94(3) EPC, Application No. 08767439.9, dated Mar. 15, 2011.
Canadian Intellectual Property Office, Requisition by the Examiner, Application No. 2,635,616, Dated Feb. 21, 2011.
European Seach Report, Application No. 11151769-4, dated Feb. 8, 2011.
Australian Office Action, Application No. 2006291165 dated Aug. 23, 2011.
European Communication Pursuant to Article 94(3) EPC, Application No. 07810382.7, dated Dec. 8, 2010.
Canadian Office Action, Application No. 2,621,441, dated Feb. 1, 2011.
EP Search Report, Application No. 08782609.5 dated Oct. 28, 2010.
Chinese Office Action, Application No. 200780040146.7 dated May 25, 2011.
Chinese Office Action, Application No. 200780005821.2 dated Jan. 26, 2011.
European Search Report, Application No. 08713330.2, dated Jul. 22, 2011.
Chinese Office Action, Application No. 200680039776.8 dated Jun. 30, 2011.
European Search Report, Applciation No. 09713926.5 dated Jul. 21, 2011.
European Search Report, Application No. 11151771-0, dated Feb. 8, 2011.
European Seach Report, Application No. 09714868.8 dated Aug. 1, 2011.
Chinese Office Action, Application No. 200680036598.3 dated Feb. 24, 2011.
European Search Report, Application No. 11151772-8, dated Feb. 8, 2011.
Alvarez-Secord, A. et al., "Maspin Expression in Epithelial Ovarian Cancer and Associations with Poor Prognosis: A Gynecologic Oncology Group Study," Gynecologic Oncology, 2006, pp. 390-397, vol. 101.
Ambros, V. et al., "A Uniform System for MicroRNA Annotation," RNA, 2003, pp. 277-279, vol. 9.
Baira, E. et al., "Ultraconserved Elements: Genomics, Function and Disease," RNA Biology, Jul. 2008, pp. 132-134, vol. 5, No. 3.
Bloomston, M. et al., "MicroRNA Expression Patterns to Differentiate Pancreatic Adenocarcinoma from Normal Pancreas and Chronic Pancreatitis," JAMA, May 2007, pp. 1901-1908 vol. 297, No. 1.
Blum, W. et al., "Clinical Response and miR-29b Predictive Significance in Older AML Patients Treated With a 10-Day Schedule of Decitabine," PNAS, Apr. 2010, pp. 7473-7478, vol. 107, No. 16.
Boland, C.R. et al., "Lynch Syndrome: Form, Function, Proteins, and Basketball," Gastroenterology, Aug. 2005, pp. 751-755, vol. 129, No. 2.
Caldas, C. et al., "Sizing Up miRNAs as Cancer Genes," Nature Medicine, Jul. 2005, pp. 712-714, vol. 11, No. 7.
Cannistra, S.A., "Cancer of the Ovary," The New England Journal of Medicine, 2004, pp. 2519-2529, vol. 351, No. 25.
Castoldi, M. et al., "A Sensitive Array for MicroRNA Expression Profiling (miChip) Based on Locked Nucleic Acids (LNA)," RNA, 2006, pp. 913-920, vol. 12.
Chim, S.S.C. et al., "Detection and Characterization of Placental MicroRNAs in Maternal Plasma," Clinical Chemistry, 2008, pp. 482-490, vol. 54, No. 3.
Cui, S. et al., "MicroRNAs that Underlie Ovarian Cancer Development and Response to Chemotherapy," 98th AACR Annual Meeting, Apr. 14-18, 2007, Los Angeles, CA.
Davies, B.R. et al., "AZD6244 (ARRY-142886), a Potent Inhibitor of Mitogen-Activated Protein Kinase/Extracellular Signal-Regulated Kinase Kinase ½ Kinases: Mechanism of Action in vivo, Pharmacokinetic/Pharmacodynamic Relationship, and Potential for Combination in Preclinical Needs," Mol. Cancer Ther., Aug. 2007, vol. 6, No. 8, pp. 2209-2219.
Debernardi, S. et al., "MicroRNA miR-181a Correlates with Morphological Sub-Class of Acute Myeloid Leukemia and the Expression of its Target Genes in Global Genome-Wide Analysis," Leukemia, 2007, pp. 912-916, vol. 21.
Esquela-Kerscher, A. et al., "Oncomirs—MicroRNAs with a Role in Cancer," Nature Reviews:Cancer, Apr. 2006, pp. 259-269, vol. 6.
Felli, N. et al., "MicroRNAs 221 and 222 Inhibit Normal Erythropoiesis and Erythroleukemic Cell Growth via Kit Receptor Down-Modulation," PNAS, Dec. 2005, pp. 18081-18086, vol. 102, No. 50.
Feng, G. et al., "Elevated Serum-Circulating RNA in Patients with Conventional Renal Cell Cancer," Anticancer Research, 2008, pp. 321-326, vol. 28.

Flavin, RJ et al., "MicroRNA Gene Expression Profiling in Human Ovarian and Primary Peritoneal Serous Carcinomas" USCAP 96th Annual Meeting, Abstract #897, San Diego, CA, Mar. 2007.
Ford, L.P., "A MicroRNA Expression Signature of Human Solid Tumors Defines Cancer Gene Targets," Leukemia Research, 2006, pp. 511-513, vol. 30.
Garofalo, M. et al., "miR-221&222 Regulate TRAIL Resistance and Enhance Tumorigenicity through PTEN and TIMP3 Downregulation," Cancer Cell, Dec. 2009, pp. 498-509, vol. 16.
Garzon, R. et al., "MicroRNA Expression and Function in Cancer," TRENDS in Molecular Medicine, Oct. 2006, pp. 580-587, vol. 12, No. 12.
Garzon, R. et al., "MicroRNA Signatures Associated with Cytogenetics and Outcome in Acute Myeloid Leukemia," ASH Annual Meeting Abstracts, Nov. 2006, Abstract #151, Part 1, p. 498, vol. 108, Issue 11.
Griffths-Jones, S. et al., "miRBase: Tools for MicroRNA Genomics," Nucleic Acids Research, 2008, pp. D154-D157, vol. 36.
Griffths-Jones, S., "The MicroRNA Registry," Nucleic Acids Research, 2004, pp. D109-D111, vol. 32.
He, L. et al., "A MicroRNA Polycistron as a Potential Human Oncogene," Nature, Jun. 2005, pp. 828-833, vol. 435.
He, X. et al., "MicroRNA and Esophageal Carcinoma," Journal of Nanjing Medical University, 2007, pp. 201-206, vol. 21, No. 4.
Ishii, H. et al., "Effect of Adenoviral Transduction of the Fragile Histidine Triad Gene into Esophageal Cancer Cells," Cancer Research, Feb. 2001, pp. 1578-1584, vol. 61.
Jacobs, I.J. et al., "Prevalence Screening for Ovarian Cancer in Postmenopausal Women by CA 125 Measurement and Ultrasonography," BMJ, Apr. 1993, pp. 1030-1034, vol. 306.
Jacobs, I.J. et al., "Progress and Challenges in Screening for Early Detection of Ovarian Cancer," Molecular & Cellular Proteomics, 2004, pp. 355-366, vol. 3.
Jemal, A. et al., "Cancer Statistics, 2008," CA Cancer J. Clin., 2008, pp. 71-96, vol. 58, No. 2.
Kelly, L.M. et al., "CT53518, A Novel Selective FLT3 Antagonist for the Treatment of Acute Myelogenous Leukemia (AML)," Cancer Cell, Jun. 2002, pp. 421-432, vol. 1.
Kozomara, A. et al., "miRBase: Integrating MicroRNA Annotation and Deep-Sequencing Data," Nucleic Acids Research, 2011, pp. D152-D157, vol. 39.
Lagos-Quintana, M. et al., "Identification of Tissue-Specific MicroRNAs from Mouse," Current Biology, Apr. 2002, pp. 735-739, vol. 12.
Landgraf, P. et al., "A Mammalian MicroRNA Expression Atlas Based on Small RNA Library Sequencing," Cell, Jun. 2007, pp. 1401-1414, vol. 129.
Lanza, G. et al., "mRNA/microRNA Gene Expression Profile in Microsatellite Unstable Colorectal Cancer," Molecular Cancer, 2007, pp. 1-11, vol. 6, No. 54.
Lawrie, C.H. et al., "Detection of Elevated Levels of Tumour-Associated MicroRNAs in Serum of Patients with Diffuse Large B-Cell Lymphoma," British Journal of Haematology, 2008, pp. 672-675, vol. 141.
Li, S.-C. et al., "Bioinformatic Discovery of MicroRNA Precursors from Human ESTs and Introns," BMC Genomics, 2006, vol. 7.
Li, Z. et al., "Inhibition of PRL-3 Gene Expression in Gastric Cancer Cell Line SGC7901 via MicroRNA Suppressed Reduces Peritoneal Metastasis," Biochemical and Biophysical Reasearch, Sep. 2006, pp. 229-237, vol. 348, No. 1.
Lujambio, A. et al., "A MicroRNA DNA Methylation Signature for Human Cancer Metastasis," PNAS, Sep. 2008, pp. 13556-13561, vol. 105, No. 36.
Medina, P.P. et al., "OncomiR Addiction in an In Vivo Model of MicroRNA-21-Induced Pre-B-Cell Lymphoma," Nature Letters, Sep. 2010, pp. 86-91, vol. 467.
Medina, P.P., "OncomiR Addicton in an in vivo Model of MicroRNA-21-Induced Pre-B-Cell Lymphoma," Supplementary Information, Sep. 2010, p. 1-22.
Mendell, J.T., "miRiad Roles for the miR-17-92 Cluster in Development and Disease," Cell, 2008, pp. 217-.
Meng, F. et al., "MicroRNA-21 Regulates Expression of the PTEN Tumor Suppressor Gene in Human Hepatocellular Cancer," Gastroenterology, 2007, pp. 647-658, vol. 133.
Naegeli, K. et al., "Novel Mechanisms of Ovarian Cancer Growth Inhibition, via MicroRNA Downregulation and Oxidative Damage, by a Ratioanlly Designed Histone Deacetylase Inhibitor," Abstract #2475, 98th ACCR Annual Meeting, Apr. 14-18, 2007, Los Angeles, CA.
Nam, E.J. et al., "MicroRNA Expression Profiles in Serous Ovarian Carcinoma," Clinical Cancer Research, 2008, pp. 2690-2695, vol. 14, No. 9.
Nicoloso, M.S. et al., "MicroRNAs—The Micro Steering Wheel of Tumour Metastases," Nature Reviews: Cancer, Apr. 2009, pp. 293-302, vol. 9.
Nurden, A.T., "Qualitative Disorders of Platelets and Megakaryocytes," Journal of Thrombosis and Haemostasis, 2005, vol. 3, pp. 1773-1782.
Olivier, R.I. et al., "CA125 and Transvaginal Ultrasound Monitoring in High-Risk Women Cannot Prevent the Diagnosis of Advanced Ovarian Cancer," Gynecologic Oncology, 2006, pp. 20-26, vol. 100.
Pichiorri, F. et al., "MicroRNAs Regulate Critical Genes Associated with Multiple Myeloma Pathogenesis," PNAS, Sep. 2008, pp. 12885-12890, vol. 105, No. 35.
Pineau, P. et al., "miR-221 Overexpression Contributes to Liver Tumorigenesis," PNAS, Jan. 2010, pp. 264-269, vol. 107, No. 1.
Porkka, K.P. et al., "MicroRNA Expression Profiling in Prostate Cancer," Cancer Research, 2007, pp. 6130-6135, vol. 67, No. 13.
Pruitt, K.D. et al., "NCBI Reference Sequence (RefSeq): A Curated Non-Redundant Sequence Database of Genomes, Transcripts and Proteins," Nucleic Acids Research, 2005, pp. D501-D504, vol. 33.
Saini, H. K. et al., "Annotation of Mammalian Primary MicroRNAs," BMC Genomics, 2008, vol. 9.
Saito, Y. et al., "Specific Activation of MicroRNA-127 with Downregulation of the Proto-Oncogene BCL6 by Chromatin-Modifying Drugs in Human Cancer Cells," Cancer Cell, Jun. 2006, pp. 435-443, vol. 9.
Santanam, U. et al., "Chronic Lymphocytic Leukemia Modeled in Mouse by Targeted miR-29 Expression," PNAS, Jul. 2010, pp. 12210-12215, vol. 107, No. 27.
Sasaki, Y.T.F. et al., "Coordinated Expression of ncRNAs and HOX mRNAs in the Human HOXA Locus," Biochemical and Biophysical Communications, 2007, pp. 724-730, vol. 357.
Schagen, F. et al., "Genetic Targeting of Adenovirus Vectors Using a Reovirus Sigmal-Based Attachment Protein," Molecular Therapy, May 2006, pp. 997-1005, vol. 13, No. 5.
Schetter, A.J. et al., "Association of Inflammation-Related and MicroRNA Gene Expression with Cancer Specific Mortality of Colon Adenocarcinoma," Clin. Cancer Res., Sep. 2009, pp. 5878-5887, vol. 15, No. 18.
Slack, F.J., "Big Roles for Small RNAs," Nature, Feb. 2010, p. 616, vol. 463.
Suarez-Saiz, F.J., "MicroRNA Expression Profiling in Acute Myelogenous Leukemia," Canada Blood, Nov. 2004, Abstract #1131, p. 320A.
Taccioli, C. et al., "Ucbase & miRfunc: A Database of Ultraconserved Sequences and MicroRNA Function," Nucleic Acids Research, 2009, pp. D41-D48, vol. 37.
Taylor, D.D. et al., "MicroRNA Signatures of Tumor-Derived Exosomes as Diagnostic Biomarkers of Ovarian Cancer," Gynecologic Oncology, 2008, pp. 13-21, vol. 110.
Thomson, M., Supplementary data for "A Custon Microarray Platform for Analysis of MicroRNA Gene Expression," Nature Methods, Oct. 2004, pp. 47-53, vol. 1, No. 1.
Tilt, E. et al., "Expression and Function of Micro RNAs in Immune Cells During Normal or Disease State," International Journa of Medicine Sciences, 2008, pp. 73-79, vol. 5, No. 2.
Uil, T.G. et al., "Generation of an Adenoviral Vector Containing an Addition of a Heterologous Ligand to the Serotpe 3 Fiber Knob," Cancer Gene Therapy, Feb. 2003, pp. 121-124, vol. 10, No. 2.
Valeri, N. et al., "Modulation of Mismatch Repair and Genomic Stability by miR-155," PNAS, Apr. 2010, pp. 6982-6987, vol. 107, No. 15.
Verschuur, A.C., "Acute Megakaryoblastic Leukemia," May 2004, pp. 1-5, Retrieved from the Internet: URL: http://www.orpga.net/data/patho/GB/uk-AMLM7.pdf.

Wijermans, P.W., "Low Dose Azanucleosidesfor High Risk (s) MDS and AML," Haematologica Reports,Nov. 2006, pp. 74-76. vol. 2, Issue, 15.

Zawacka-Pankau, J. et al., "Expression and Simple, One-Step Purification of Fragile Histidine Triad (Fhit) Tumor Suppressor Mutant Forms in *Escherichia coli* and their Interaction with Protoporphyrin IX," Biotechnology Letters, Jun. 2007, pp. 877-883, vol. 29, No. 6.

Budhu, et al., Identification of Metastasis-Related MicroRNA's in Hepatocellular Carcinoma, Hepatology, Mar. 2008, pp. 897-907, vol. 47.

Budhu, et al., A Unique Metastasis-Related MicroRNA Expression Signature is a Prognostic Indicator of Survival and Recurrence in Hepatocellular Carcinoma, Oct. 2007, p. 791A, vol. 46, No. 4.

Kutay, et al., Downregulation of miR-122 in the Rodent and Human Hepatocellular Carinomas, Journal of Cellular Biochemistry, 2006, pp. 671-678, vol. 99.

Lu, et al., MicroRNA expression profiles classify human cancers, Nature, Jun. 2005, pp. 834-838, vol. 435/9.

Thorgeirsson, et al., Functional Genomics of Hepatocellular Carcinoma, Hepatology, 2006, pp. S145-S150, vol. 43.

Yanaihara, et al., Unique microRNA molecular profiles in lung cancer diagnosis and prognosis, Cancer Cell, Mar. 2006, pp. 189-198, vol. 9.

European Patent Office Communication, Nov. 24, 2009, PCT/US2007023660.

State Intellectual Property Office of the People's Republic of China, Notification of the First Office Action, Application No. 200780005791.5, dated Mar. 24, 2011.

Akahoshi, M. et al., "Myeloproliferative Disorders Terminating in Acute Megakaryoblastic Leukemia with Chromosome 3q26 Abnormality," Cancer, 1987, pp. 2654-2661, vol. 60.

Akao, Y. et al., "let-7 MicroRNA Functions as a Potential Growth Suppressor in Human Colon Cancer Cells," Biol. Pharm. Bull., May 2006, pp. 903-906, vol. 29, No. 5.

Ambs, S. et al., "Genomic Profiling of MicroRNA and Messenger RNA Reveals Deregulated MicroRNA Expression in Prostate Cancer," Cancer Research, Aug. 2008, pp. 6162-6170, vol. 68, No. 15.

Aqeilan, R. I. et al., "Targeted Deletion of WWOX Reveals a Tumor Suppressor Function," PNAS, Mar. 2007, pp. 3949-3954, vol. 104, No. 10.

Bandres, E. et al., "Identification by Real-Time PCR of 13 Mature MicroRNAs Differentially Expressed in Colorectal Cancer and Non-Tumoral Tissues," Molecular Cancer, Jul. 2006, 10 pages, vol. 5, No. 29.

Bartel, D. P., "MicroRNAs: Target Recognition and Regulatory Functions," Cell, Jan. 2009, pp. 215-233, vol. 136.

Bednarek, A. K. et al., "WWOX, the FRA16D Gene, Behaves as a Suppressor of Tumor Growth," Cancer Research, Nov. 2001, pp. 8068-8073, vol. 61.

Bejenaro, etal., "Ultraconserved Elements in the Human Genome," Electronic Suppl. Data, Science, 2004.

Bejerano, G. et al., "Ultraconserved Elements in the Human Genome," Science, May 2004, pp. 1321-1325, vol. 304.

Bell, D. A., "Origins and Molecular Pathology of Ovarian Cancer," Modern Pathology, 2005, pp. S19-S32, vol. 18.

Bichi, R. et al., "Human Chronic Lymphocytic Leukemia Modeled in Mouse by Targeted TCL1 Expression," PNAS, May 2002, pp. 6955-6960, vol. 99, No. 10.

Brueckner, B. et al., "The Human let-7a-3 Locus Contains an Epigenetically Regulated MicroRNA Gene with Oncogenic Function," Cancer Research, Feb. 2007, pp. 1419-1423, vol. 67, No. 4.

Budhu, A. et al., "A Unique Metastasis-Related MicroRNA Expression Signature is a Prognostic Indicator of Survival and Recurrence in Hepatocellular Carcinoma," Hepatology, 2007, p. 791A, vol. 46, No. 4, Suppl. 1, Abstract #1249.

Budhu, A. et al., "Identification of Metastasis-Related MicroRNAs in Hepatocellular Carcinoma," Hepatology, Mar. 2008, pp. 897-907, vol. 47, No. 3.

Calin, G. A. et al., "A MicroRNA Signature Associated with Prognosis and Progression in Chronic Lymphocytic Leukemia," The New England Journal of Medicine, Oct. 2005, pp. 1793-1801, vol. 353, No. 17.

Calin, G. A. et al., "Chromosomal Rearrangements and MicroRNAs: A New Cancer Link with Clinical Implications," the Journal of Clinical Investigation, Aug. 2007, pp. 2059-2066, vol. 117, No. 8.

Calin, G. A. et al., "Frequent Deletions and Down-Regulation of MicroRNA Genes miR15 and miR16 at 13q14 in Chronic Lymphocytic Leukemia," PNAS, Nov. 2002, pp. 15524-15529, vol. 99, No. 24.

Calin, G. A. et al., "Human MicroRNA Genes are Frequently Located at Fragile Sites and Genomic Regions Involved in Cancers," PNAS, Mar. 2004, pp. 2999-3004, vol. 101, No. 9.

Calin, G. A. et al., "MicroRNA Profiling Reveals Distinct Signatures in B Cell Chronic Lymphocytic Leukemias," PNAS, Aug. 2004, pp. 11755-11760, vol. 101, No. 32.

Calin, G. A. et al., "MicroRNA Signatures in Human Cancers," Nature Reviews Cancer, Nov. 2006, pp. 857-866, vol. 6.

Calin, G. A. et al., "MiR-15a and MiR-16-1 Cluster Functions in Human Leukemia," PNAS, Apr. 2008, pp. 5166-5171, vol. 105, No. 13.

Calin, G. A. et al., "Ultraconserved Regions Encoding ncRNAs are Altered in Human Leukemias and Carcinomas," Cancer Cell, Sep. 2007, pp. 215-229, vol. 12.

Chan, J. A. et al., "MicroRNA-21 is an Antiapoptotic Factor in Human Glioblastoma Cells," Cancer Research, Jul. 2005, pp. 6029-6033, vol. 65, No. 14.

Chang, N.-S. et al., "Molecular Mechanisms Underlying WOX1 Activation During Apoptotic and Stress Responses," Biochemical Pharmacology, 2003, pp. 1347-1354, vol. 66.

Chang, T.-C. et al., "Widespread MicroRNA Repression by Myc Contributes to Tumorigenesis," Nat Genet., Jan. 2008, pp. 43-50, vol. 40, No. 1.

Chen, C.-Z. et al., "MicroRNAs as Regulators of Mammalian Hematopoiesis," Seminars in Immunology, 2005, pp. 155-165, vol. 17.

Cheng, A. M. et al., "Antisense Inhibition of Human miRNAs and Indications for an Involvement of miRNA in Cell Growth and Apoptosis," Nucleic Acids Research, 2005, pp. 1290-1297, vol. 33, No. 4.

Ciafre, S. A. et al., "Extensive Modulation of a Set of MicroRNAs in Primary Glioblastoma," Biochemical and Biophysical Research Communications, 2005, pp. 1351-1358, vol. 334.

Cimmino, A. et al., "miR-15 and miR-16 Induce Apoptosis by Targeting BCL2," PNAS, Sep. 2005, pp. 13944-13949, vol. 102, No. 39.

Cimmino, A. et al., Corrections to "miR-15 and miR-16 Induce Apoptosis by Targeting BCL2," PNAS, Feb. 2006, pp. 2464-2465, vol. 103, No. 7.

Costinean, S. et al., "Pre-B Cell Proliferation and Lymphoblastic Leukemia/ High-Grade Lymphoma in Eµ-miR155 Transgenic Mice," PNAS, May 2006, pp. 7024-7029, vol. 103, No. 18.

Croce, C. M. et al., "miRNAs, Cancer, and Stem Cell Division," Cell, 2005, pp. 6-7, vol. 36.

Croce, C. M. et al., "Role of FHIT in Human Cancer," Journal of Clinical Oncology, May 1999, pp. 1618-1624, vol. 17, No. 5.

Croce, C. M., "Causes and Consequences of MicroRNA Dysregulation in Cancer," Nature Reviews Genetics, Oct. 2009, pp. 704-714, vol. 10.

Croce, C. M., "Oncogenes and Cancer," The New England Journal of Medicine, Jan. 2008, pp. 502-511, vol. 358, No. 5.

Dalmay, T. et al., "MicroRNAs and the Hallmarks of Cancer," Oncogene, 2006, pp. 6170-6175, vol. 25.

Davies, F. E. et al., "Insights into the Multistep Transformation of MGUS to Myeloma Using Microarray Expression Analysis," Blood, Dec. 2003, pp. 4504-4511, vol. 102, No. 13.

Dohner, H. et al., "Genomic Aberrations and Survival in Chronic Lymphocytic Leukemia," The New England Journal of Medicine, Dec. 2000, pp. 1910-1916, vol. 343, No. 26.

Druck, etal., "FHIT," Atlas of Genetics and Cytogenetics in Oncology and Haematology, 2007, pp. 171-178, vol. 2.

Eis, P. S. et al., "Accumulation of miR-155 and BIC RNA in Human B Cell Lymphomas," PNAS, Mar. 2005, pp. 3627-3632, vol. 102, No. 10.

European Patent Application, EP 1795203 A2, Croce et al., Application No. 06010581.4, filed Feb. 7, 1997, published Jun. 13, 2007.

European Search Report, Application No. 06800599.0 dated Oct. 19, 2009.
European Search Report, Application No. 06814375.9 dated Oct. 8, 2009.
European Search Report, Application No. 06825457.2 dated Sep. 16, 2009.
European Search Report, Application No. 07716208.9 dated Nov. 10, 2009.
European Search Report, Application No. 07717734.3 dated Nov. 9, 2009.
European Search Report, Application No. 07717903.4 dated Oct. 23, 2009.
European Search Report, Application No. 07753450.1 dated Jan. 12, 2009.
European Search Report, Application No. 07810382.7 dated Sep. 14, 2009.
European Search Report, Application No. 07867402.5 dated Mar. 16, 2010.
European Search Report, Application No. 07872618.9 dated Jul. 5, 2010.
European Search Report, Application No. 08767439.6 dated May 12, 2010.
European Search Report, Application No. 08768266.2 dated Jul. 1, 2010.
European Search Report, Application No. 08796821.0 dated Aug. 4, 2010.
European Search Report, Application No. 08841700.1 dated Jun. 2, 2010.
Fabbri, M. et al., "MicroRNA-29 Family Reverts Aberrant Methylation in Lung Cancer by Targeting DNA Methyltransferases 3A and 3B," PNAS, Oct. 2007, pp. 15805-15810, vol. 104, No. 40.
Fabbri, M. et al., "MicroRNAs," The Cancer Journal, Jan./Feb. 2008, pp. 1-6, vol. 14, No. 1.
Fabbri, M. et al., "WWOX Gene Restoration Prevents Lung Cancer Growth In Vitro and In Vivo," PNAS, Oct. 2005, pp. 15611-15616, vol. 102, No. 43.
Fong, Y. et al., "Muir-Torre-Like Syndrome in FHIT-Deficient Mice," PNAS, Apr. 2000, pp. 4742-4747, vol. 97, No. 9.
Fox, T. et al., "A Single Amino Acid Substitution Makes ERK2 Susceptible to Pyridinyl Imidazole Inhibitors of p38 Map Kinase," Protein Science, 1998, pp. 2249-2255, vol. 7.
Garzon, et al., "MicroRNA 29b Functions in Acute Myeloid Leukemia," Prepublished Online, www.bloodjournal.org, Oct. 2009, doi:10.1182/blood-2009-03-211938, pp. 5331-5341, vol. 114.
Garzon, R. et al., "MicroRNA Fingerprints During Human Megakaryocytopoiesis," PNAS, Mar. 2006, pp. 5078-5083, vol. 103, No. 13.
Garzon, R. et al., "MicroRNA Signatures Associated with Cytogenetics and Prognosis in Acute Myeloid Leukemia," Blood, Published Online Jan. 2008, DOI: 10.1182/blood-2007-07-098749.
Godlewski, J. et al., "Targeting of the Bmi-1 Oncogene/Stem Cell Renewal Factor by MicroRNA-128 Inhibits Glioma Proliferation and Self-Renewal," Cancer Research, Nov. 2008, pp. 9125-9130, vol. 68, No. 22.
Gourley, C. et al., "WWOX Gene Expression Abolishes Ovarian Cancer Tumorigenicity In Vivo and Decreases Attachment to Fibronectin via Integrin α3," Cancer Research, Jun. 2009, pp. 4835-4842, vol. 69, No. 11.
Griffiths-Jones, S. et al., "miRBase: MicroRNA Sequences, Targets and Gene Nomenclature," Nucleic Acids Research, 2006, pp. D140-D144, vol. 34.
Guimaraes-Sternberg, C. et al., "MicroRNA Modulation of Megakaryoblast Fate Involves Cholinergic Signaling," Leukemia Research, 2006, pp. 583-595, vol. 30.
Guweidhi, A. et al. "Enhanced Expression of 14-3-3sigma in Pancreatic Cancer and its Role in Cell Cycle Regulation and Apoptosis," Carcinogenesis, 2004, pp. 1575-1585, vol. 25, No. 9.
Havelange, V. et al., "MicroRNAs: New Players in Acute Myeloid Leukemia," British Journal of Cancer, 2009, pp. 743-748, vol. 101.
Hayashita, Y. et al., "A Polycistronic MicroRNA Cluster, miR-17-92, is Overexpressed in Human Lung Cancers and Enhances Cell Proliferation," Cancer Research, Nov. 2005, pp. 9628-9632, vol. 65, No. 21.

Herling, et al., "TCL1 Shows a Regulated Expression Pattern in Chronic Lymphocytic Leukemia that Correlates with Molecular Subtypes and Proliferative State," Leukemia, Feb. 2006, pp. 280-285, vol. 20, No. 2.
Hiromura, M. et al., "Identification of Nerve Growth Factor-Responsive Element of the TCL1 Promoter as a Novel Negative Regulatory Element," The Journal of Biological Chemistry, Sep. 2006, pp. 27753-27764, vol. 281, No. 38.
Huang, Y.-S. et al., "Microarray Analysis of MicroRNA Expression in Hepatocellular Carcinoma and Non-Tumorous Tissues Without Viral Hepatitis," Journal of Gastroenterology and Hepatology, 2008, pp. 87-94, vol. 23.
Iliopoulos, D. et al., "Fragile Genes as Biomarkers: Epigenetic Control of WWOX and FHIT in Lung, Breast and Bladder Cancer," Oncogene, 2005, pp. 1625-1633, vol. 24.
Iliopoulos, D. et al., "Inhibition of Breast Cancer Growth In Vitro and In Vivo: Effect of Restoration of WWOX Expression," Clin. Cancer Research, Jan. 2007, pp. 268-274, vol. 13, No. 1.
Iorio, M. V. et al., "MicroRNA Gene Expression Deregulation in Human Breast Cancer," Cancer Research, Aug. 2005, pp. 7065-7070, vol. 65, No. 16.
Iorio, M. V. et al., "MicroRNA Signatures in Human Ovarian Cancer," Cancer Research, Sep. 2007, pp. 8699-8707, vol. 67, No. 18.
Ivanovska, I. et al., "MicroRNAs in the miR-106b Family Regulate p21/CDKN1A and Promote Cell Cycle Progression," Molecular and Cellular Biology, Apr. 2008, pp. 2167-2174, vol. 28, No. 7.
Jansen, A. P. et al., "Epidermal Expression of the Translation Inhibitor Programmed Cell Death 4 Suppresses Tumorigenesis," Cancer Research, Jul. 2005, pp. 6034-6041, vol. 65, No. 14.
Ji, J. et al., "MicroRNA Expression, Survival, and Response to Interferon in Liver Cancer," The New England Journal of Medicine, Oct. 2009, pp. 1437-1447, vol. 361, No. 15.
Ji, J. et al., "New Kids on the Block: Diagnostic and Prognostic MicroRNAs in Hepatocellular Carcinoma," Cancer Biology & Therapy, Aug. 2009, pp. 1-8, vol. 8, No. 16.
Ji, L. et al., "Induction of Apoptosis and Inhibition of Tumorigenicity and Tumor Growth by Adenovirus Vector-Mediated Fragile Histidine Triad (FHIT) Gene Overexpression," Cancer Research, Jul. 1999, pp. 3333-3339, vol. 59.
Jiang, J. et al., "Association of MicroRNA Expression in Hepatocellular Carcinomas with Hepatitis Infection, Cirrhosis, and Patient Survival," Clin Cancer Research, Jan. 2008, pp. 419-427, vol. 14, No. 2.
Jiang, J. et al., "Real-Time Expression Profiling of MicroRNA Precursors in Human Cancer Cell Lines," Nucleic Acids Research, 2005, pp. 5394-5403, vol. 33, No. 17.
John, B. et al., "Human MicroRNA Targets," PLOS Biology, Nov. 2004, pp. 1862-1879, vol. 2, Issue 11.
Johnson, S. M. et al., "RAS is Regulated by the let-7 MicroRNA Family," Cell, Mar. 2005, pp. 635-647, vol. 120.
Johnson, S. M. et al., "RAS is Regulated by the let-7 MicroRNA Family," Supplemental Data, Cell, Mar. 2005, pp. 635-647, vol. 120.
Kawasaki, H. et al., "MicroRNA-196 Inhibits HOXB8 Expression in Myeloid Differentiation of HL60 Cells," Nucleic Acids Symposium Series, 2004, pp. 211-212, No. 48.
Kim, H. et al., "Elevated mRNA Levels of DNA Methyltransferase-1 as an Independent Prognostic Factor in Primary Nonsmall Cell Lung Cancer," Cancer, Sep. 2006, pp. 1042-1049, vol. 107, No. 5.
Kotoula, V. et al., "In Situ Detection of MicroRNAs 146b, 221 and 222 in Human Carcinoma Tissues Reveals Tumor-Type Specific Expression Patterns," In: Proceedings of the 98th Annual Meeting of the American Association for Cancer Research, Apr. 14-18, 2007, Los Angeles, CA: AACR, 2007, 2 pages, Abstract No. 1780.
Koturbash, I. et al., "Role of Epigenetic Effectors in Maintenance of the Long-Term Persistent Bystander Effect in Spleen In Vivo," Carcinogenesis, 2007, pp. 1831-1838, vol. 28, No. 8.
Krek, A. et al., "Combinatorial MicroRNA Target Predictions," Nature Genetics, May 2005, pp. 495-500, vol. 37, No. 5.
Kulshreshtha, R. et al., "A MicroRNA Signature of Hypoxia," Molecular and Cellular Biology, Mar. 2007, pp. 1859-1867, vol. 27, No. 5.

Kuroki, et al., "Genetic Alterations of the Tumor Suppressor Gene WWOX in Esophageal Squamous Cell Carcinoma," Cancer Research, Apr. 2002, pp. 2258-2260, vol. 62.
Kutay, H. et al., "Downregulation of miR-122 in the Rodent and Human Hepatocellular Carcinomas," Journal of Cellular Biochemistry, 2006, pp. 671-678, vol. 99.
Lagos-Quintana, M. et al., "New MicroRNAs From Mouse to Human," RNA, 2003, pp. 175-179, vol. 9, No. 2.
Landi, M. T. et al., "Gene Expression Signature of Cigarette Smoking and its Role in Lung Adenocarcinoma Development and Survival," PLOS One, Feb. 2008, pp. 1-8, vol. 3, Issue 2.
Lee, E. J. et al., "Expression Profiling Identifies MicroRNA Signature in Pancreatic Cancer," Int. J. Cancer, 2006, pp. 1046-1054, vol. 120.
Lewis, B. P. et al., "Prediction of Mammalian MicroRNA Targets," Cell, Dec. 2003, pp. 787-798, vol. 115.
Lin, R.-K. et al., "Alteration of DNA Methyltransferases Contributes to 5'CpG Methylation and Poor Prognosis in Lung Cancer," Lung Cancer, 2007, pp. 205-213, vol. 55.
Lipp, E., "MicroRNAs Inform Cancer Research: Alterations in the Expression of miRNA Genes Contribute to Pathogenesis on Broad Basis," Genetic Engineering & Biotechnology News, Dec. 2009, pp. 38-39, genengnews.com.
Liu, C.-G. et al., "An Oligonucleotide Microchip for Genome-Wide MicroRNA Profiling in Human and Mouse Tissues," PNAS, Jun. 2004, pp. 9740-9744, vol. 101, No. 26.
Lu, J. et al., "MicroRNA Expression Profiles Classify Human Cancers," Nature, Jun. 2005, pp. 834-838, vol. 435, Supplementary Information.
Lu, J. et al., "MicroRNA Expression Profiles Classify Human Cancers," Nature, Jun. 2005, pp. 834-838, vol. 435.
Ma, G. et al., "Expression of Programmed Cell Death 4 and its Clinicopathological Significance in Human Pancreatic Cancer," Department of General Surgery, the First Affiliated Hospital, China Medical University, Oct. 2005, pp. 597-600.
Mack, G. S., "MicroRNA Gets Down to Business," Nature Biotechnology, Jun. 2007, pp. 631-638, vol. 25, No. 6.
Marchetti, A. et al., "EGFR Mutations in Non-Small-Cell Lung Cancer: Analysis of a Large Series of Cases and Development of a Rapid and Sensitive Method for Diagnostic Screening with Potential Implications on Pharmacologic Treatment," Journal of Clinical Oncology, Feb. 2005, pp. 857-865, vol. 23, No. 4.
Marcucci, et al., "MicroRNA Expression in Cytogenetically Normal Acute Myeloid Leukemia," NEJM, May 2008, pp. 1919-1928, vol. 358, No. 18.
Mattie, M. D. et al., "Optimized High-Throughput MicroRNA Expression Profiling Provides Novel Biomarker Assessment of Clinical Prostate and Breast Cancer Biopsies," Molecular Cancer, Jun. 2006, 14 pages, vol. 5, No. 24.
McManus, M. T., "MicroRNAs and Cancer," Seminars in Cancer Biology, 2003, pp. 253-258, vol. 13.
Megraw, M. et al., "miRGen: A Database for the Study of Animal MicroRNA Genomic Organization and Function," Nucleic Acids Research, 2007, pp. D149-D155, vol. 35.
Meng, F. et al., "Involvement of Human MicroRNA in Growth and Response to Chemotherapy in Human Cholangiocarcinoma Cell Lines," Gastroenterology, 2006, pp. 2113-2129, vol. 130.
Mi, S. et al., "MicroRNA Expression Signatures Accurately Discriminate Acute Lymphoblastic Leukemia from Acute Myeloid Leukemia," PNAS, Dec. 2007, pp. 19971-19976, vol. 104, No. 50.
Michael, M. Z. et al., "Reduced Accumulation of Specific MicroRNAs in Colorectal Neoplasia," Molecular Cancer Research, Oct. 2003, pp. 882-891, vol. 1.
Miller, M. K. et al., "Concurrent Chronic Lymphocytic Leukemia Cutis and Acute Myelogenous Leukemia Cutis in a Patient with Untreated CLL," The American Journal of Dermatopathology, 2001, pp. 334-340, vol. 23, No. 4.
Mitchell, P. S. et al., "Circulating MicroRNAs as Stable Blood-Based Markers for Cancer Detection," PNAS, Jul. 2008, pp. 10513-10518, vol. 105, No. 30.
Mitrovic, T. et al., "Cancer Gene Therapy," Arch. Oncology, 2005, pp. 23-26, vol. 13, No. 1.
Mountzios, G. et al., "Mechanisms of Disease: Signal Transduction in Lung Carcinogenesis—A Comparison of Smokers and Never-Smokers," Nature Clinical Practice Oncology, Oct. 2008, pp. 610-618, vol. 5, No. 10.
Murakami, Y. et al., "Comprehensive Analysis of MicroRNA Expression Patterns in Hepatocellular Carcinoma and Non-Tumorous Tissues," Oncogene, 2006 pp. 2537-2545, vol. 25., published online Dec. 5, 2005.
Nakanishi, H. et al., "ALL1 Fusion Proteins Induce Deregulation of EphA7 and ERK Phosphorylation in Human Acute Leukemias," PNAS, Sep. 2007, pp. 14442-14447, vol. 104, No. 36.
Negrini, M. et al., "MicroRNAs in Human Cancer: From Research to Therapy," Journal of Cell Science, Apr. 2007, pp. 1833-1840, vol. 120.
Notice of Allowance and Fees Due in U.S. Appl. No. 12/160,064, filed Jul. 3, 2008, mailing date Nov. 20, 2009.
Notice of Allowance and Fees Due in U.S. Appl. No. 12/298,221, filed Nov. 10, 2008, mailing date Nov. 30, 2009.
Office Action issued in U.S. Appl. No. 12/083,067, filed Jun. 20, 2008, mailing date Jul. 8, 2010.
Office Action issued in U.S. Appl. No. 12/160,034, filed Jul. 3, 2008, mailing date Jun. 7, 2010.
Office Action issued in U.S. Appl. No. 12/160,061, filed Jul. 3, 2008, mailing date Mar. 12, 2010.
Office Action issued in U.S. Appl. No. 12/160,061, filed Jul. 3, 2008, mailing date Apr. 24, 2009.
Office Action issued in U.S. Appl. No. 12/160,061, filed Jul. 3, 2008, mailing date Oct. 30, 2009.
Office Action issued in U.S. Appl. No. 12/160,064, filed Jul. 3, 2008, mailing date Aug. 10, 2009.
Office Action issued in U.S. Appl. No. 12/293,471, filed Oct. 9, 2008, mailing date Jun. 8, 2010.
Office Action issued in U.S. Appl. No. 12/373,358, filed Feb. 11, 2009, mailing date Aug. 20, 2010.
Office Action issued in U.S. Appl. No. 12/442,018, filed Mar. 27, 2009, mailing date Apr. 15, 2010.
Palamarchuk, A. et al., "Akt Phosphorylates Tcl1 Oncoprotein and Inhibits its Repressor Activity," Cancer Research, Jun. 2005, pp. 4515-4519, vol. 65, No. 11.
Pawelczyk, T. et al., "Expression in *Escherichia coli* and Simple Purification of Human Fhit Protein," Protein Expr. Purlf., Apr. 2000, pp. 320-326, vol. 18, No. 3.
PCT International Preliminary Report on Patentability, PCT/US/2007/023660 filed Nov. 1, 2007, dated May 5, 2009.
PCT International Preliminary Report on Patentability, PCT/US/2008/072081 filed Aug. 4, 2008, dated Feb. 9, 2010.
PCT International Preliminary Report on Patentability, PCT/US2006/029889 filed Jul. 31, 2006, dated Feb. 5, 2008.
PCT International Preliminary Report on Patentability, PCT/US2006/035100 filed Sep. 11, 2006, dated Mar. 18, 2008.
PCT International Preliminary Report on Patentability, PCT/US2006/038824 filed Oct. 4, 2006, dated Apr. 9, 2008.
PCT International Preliminary Report on Patentability, PCT/US2007/000024 filed Jan. 3, 2007, dated Jul. 8, 2008.
PCT International Preliminary Report on Patentability, PCT/US2007/000103 filed Jan. 3, 2007, dated Jul. 8, 2008.
PCT International Preliminary Report on Patentability, PCT/US2007/000159 filed Jan. 3, 2007, dated Jul. 8, 2008.
PCT International Preliminary Report on Patentability, PCT/US2007/006824 filed Mar. 19, 2007, dated Sep. 23, 2008.
PCT International Preliminary Report on Patentability, PCT/US2007/009910 filed Apr. 24, 2007, dated Oct. 28, 2008.
PCT International Preliminary Report on Patentability, PCT/US2007/015892 filed Jul. 12, 2007, dated Jan. 13, 2009.
PCT International Preliminary Report on Patentability, PCT/US2007/020215 filed Sep. 17, 2007, dated Mar. 24, 2009.
PCT International Preliminary Report on Patentability, PCT/US2008/001157 filed Jan. 29, 2008, dated Aug. 4, 2009.
PCT International Preliminary Report on Patentability, PCT/US2008/005503 filed Apr. 29, 2008, dated Nov. 3, 2009.
PCT International Preliminary Report on Patentability, PCT/US2008/007196 filed Jun. 9, 2008, dated Dec. 11, 2009.

PCT International Preliminary Report on Patentability, PCT/US2008/066870 filed Jun. 13, 2008, dated Dec. 17, 2009.
PCT International Preliminary Report on Patentability, PCT/US2008/071532 filed Jul. 30, 2008, dated Feb. 2, 2010.
PCT International Preliminary Report on Patentability, PCT/US2008/073964 filed Aug. 22, 2008, dated Feb. 24, 2010.
PCT International Preliminary Report on Patentability, PCT/US2008/075565 filed Sep. 8, 2008, dated Mar. 9, 2010.
PCT International Preliminary Report on Patentability, PCT/US2008/079482 filed Oct. 10, 2008, dated Apr. 13, 2010.
PCT International Preliminary Report on Patentability, PCT/US2008/081294 filed Oct. 27, 2008, dated Apr. 27, 2010.
PCT International Preliminary Report on Patentability, PCT/US2009/035458 filed Feb. 27, 2009, dated Aug. 31, 2010.
PCT International Preliminary Report on Patentability, PCT/US2009/035463 filed Feb. 27, 2009, dated Aug. 31, 2010.
PCT International Preliminary Report on Patentability, PCT/US2009/035470 filed Feb. 27, 2009, dated Aug. 31, 2010.
PCT International Preliminary Report on Patentability, PCT/US2009/035482 filed Feb. 27, 2009, dated Aug. 31, 2010.
PCT International Search Report and the Written Opinion, PCT/US2007/006824 filed Mar. 19, 2007, dated Mar. 3, 2008.
PCT International Search Report and the Written Opinion, PCT/US2006/29889 filed Jul. 31, 2006, dated Jul. 10, 2007.
PCT International Search Report and the Written Opinion, PCT/US2006/35100 filed Sep. 11, 2006, dated Sep. 5, 2007.
PCT International Search Report and the Written Opinion, PCT/US2006/38824 filed Oct. 4, 2006, dated Aug. 9, 2007.
PCT International Search Report and the Written Opinion, PCT/US2007/00024 filed Jan. 3, 2007, dated Nov. 5, 2007.
PCT International Search Report and the Written Opinion, PCT/US2007/00103 filed Jan. 3, 2007, dated Dec. 3, 2007.
PCT International Search Report and the Written Opinion, PCT/US2007/00159 filed Jan. 3, 2007, dated Apr. 11, 2008.
PCT International Search Report and the Written Opinion, PCT/US2007/006824 filed Mar. 19, 2007, dated May 14, 2008.
PCT International Search Report and the Written Opinion, PCT/US2007/09910 filed Apr. 24, 2007, dated Feb. 13, 2008.
PCT International Search Report and the Written Opinion, PCT/US2007/15892 filed Jul. 12, 2007, dated Sep. 30, 2008.
PCT International Search Report and the Written Opinion, PCT/US2007/20215 filed Sep. 17, 2007, dated Jul. 25, 2008.
PCT International Search Report and the Written Opinion, PCT/US2007/23660 filed Nov. 1, 2007, dated Sep. 16, 2008.
PCT International Search Report and the Written Opinion, PCT/US2008/01157 filed Jan. 29, 2008, dated Aug. 7, 2008.
PCT International Search Report and the Written Opinion, PCT/US2008/05503 filed Apr. 29, 2008, dated Sep. 25, 2008.
PCT International Search Report and the Written Opinion, PCT/US2008/07196 filed Jun. 9, 2008, dated Nov. 19, 2008.
PCT International Search Report and the Written Opinion, PCT/US2008/66870 filed Jun. 13, 2008, dated Nov. 10, 2008.
PCT International Search Report and the Written Opinion, PCT/US2008/71532 filed Jul. 30, 2008, dated Apr. 17, 2009.
PCT International Search Report and the Written Opinion, PCT/US2008/72081 filed Aug. 4, 2008, dated Jan. 14, 2009.
PCT International Search Report and the Written Opinion, PCT/US2008/73964 filed Aug. 22, 2008, dated Dec. 24, 2008.
PCT International Search Report and the Written Opinion, PCT/US2008/75565 filed Sep. 8, 2008, dated Dec. 9, 2008.
PCT International Search Report and the Written Opinion, PCT/US2008/79482 filed Oct. 10, 2008, dated Dec. 22, 2008.
PCT International Search Report and the Written Opinion, PCT/US2008/81294 filed Oct. 27, 2008, dated Mar. 26, 2009.
PCT International Search Report and the Written Opinion, PCT/US2008/84821 filed Nov. 26, 2008, dated Feb. 17, 2009.
PCT International Search Report and the Written Opinion, PCT/US2009/35458 filed Feb. 27, 2009, dated Jul. 28, 2009.
PCT International Search Report and the Written Opinion, PCT/US2009/35463 filed Feb. 27, 2009, dated Aug. 13, 2009.
PCT International Search Report and the Written Opinion, PCT/US2009/35470 filed Feb. 27, 2009, dated Jun. 16, 2009.
PCT International Search Report and the Written Opinion, PCT/US2009/35482 filed Feb. 27, 2009, dated Jul. 17, 2009.
PCT International Search Report and the Written Opinion, PCT/US2009/38214 filed Mar. 25, 2009, dated Aug. 14, 2009.
PCT International Search Report and the Written Opinion, PCT/US2009/46999 filed Jun. 11, 2009, dated Nov. 23, 2009.
PCT International Search Report and the Written Opinion, PCT/US2009/53586 filed Aug. 12, 2009, dated Oct. 28, 2009.
PCT International Search Report and the Written Opinion, PCT/US2009/65072 filed Nov. 19, 2009, dated Mar. 3, 2010.
PCT International Search Report and the Written Opinion, PCT/US2010/025173 filed Feb. 24, 2010, dated Jul. 6, 2010.
Pedersen, I. M. et al., "Interferon Modulation of Cellular MicroRNAs as an Antiviral Mechanism," Nature, Oct. 2007, pp. 919-922, vol. 449.
Pekarsky, Y. et al., "Animal Models for Chronic Lymphocytic Leumekia," Journal of Cellular Biochemistry, 2007, pp. 1109-1118, vol. 100.
Pekarsky, Y. et al., "Tcl1 Enhances Akt Kinase Activity and Mediates its Nuclear Translocation," PNAS, Mar. 2000, pp. 3028-3033, vol. 97, No. 7.
Pekarsky, Y. et al., "Tcl1 Expression in Chronic Lymphocytic Leukemia is Regulated by miR-29 and miR-181," Cancer Research, Dec. 2006, pp. 11590-11593, vol. 66, No. 24.
Pekarsky, Y. et al., "Tcl1 Functions as a Transcriptional Regulator and is Directly Involved in the Pathogenesis of CLL," PNAS, Dec. 2008, pp. 19643-19648, vol. 105, No. 50.
Petrocca, F. et al., "E2F1-Regulated MicroRNAs Impair TGFβ-Dependent Cell-Cycle Arrest and Apoptosis in Gastric Cancer," Cancer Cell, Mar. 2008, pp. 272-286, vol. 13.
Prueitt, R. L. et al., "Expression of MicroRNAs and Protein-Coding Genes Associated with Perineural Invasion in Prostate Cancer," The Prostate, 2008, pp. 1152-1164, vol. 68.
Qin, H. R. et al., "A Role for the WWOX Gene in Prostate Cancer," Cancer Research, Jul. 2006, pp. 6477-6481, vol. 66, No. 13.
Ramkissoon, S. H, et al., "Hematopoietic-Specific MicroRNA Expression in Human Cells," Leukemia Research, 2006, pp. 643-647, vol. 30.
Roldo, C. et al., "MicroRNA Expression Abnormalities in Pancreatic Endocrine and Acinar Tumors Are Associated With Distinctive Pathologic Feature and Clinical Behavior," Journal of Clinical Oncology, Oct. 2006, pp. 4677-4684, vol. 24, No. 29.
Rozovskaia, T. et al., "Expression Profiles of Acute Lymphoblastic and Myeloblastic Leukemias with ALL-1 Rearrangements," PNAS, Jun. 2003, pp. 7853-7858, vol. 100, No. 13.
Schetter, A. J. et al., "MicroRNA Expression Profiles Associated With Prognosis and Therapeutic Outcome in Colon Adenocarcinoma," JAMA, Jan. 2008, pp. 425-436, vol. 299, No. 4.
Schmittgen, T. D. et al., "A High-Throughput Method to Monitor the Expression of MicroRNA Precursors," Nucleic Acids Research, Feb. 2004, vol. 32, No. 4.
Seike, M. et al., "MiR-21 is an EGFR-Regulated Anti-Apoptotic Factor in Lung Cancer in Never-Smokers," PNAS, Jul. 2009, pp. 12085-12090. vol. 106, No. 29.
Seike, M. et al., "MiR-21 is an EGFR-Regulated Anti-Apoptotic Factor in Lung Cancer in Never-Smokers," Supporting Information, PNAS, Jul. 2009, pp. 12085-12090. vol. 106, No. 29.
Seike, M., "MicroRNA Expression Profiles in Lung Cancer Cooperated with Drug Sensitivity to EGFR Tyrosine Kinase Inhibitor," J. Nippon Med. School, 2009, pp. 275-276, vol. 76, No. 5.
Seth, P., "Vector-Mediated Cancer Gene Therapy," Cancer Biology & Therapy, May 2005, pp. 512-517, vol. 4, Issue 5.
Sevinsky, J. R. et al., "Extracellular Signal-Regulated Kinase Induces the Megakaryocyte GPIIb/CD41 Gene Through MafB/Kreisler," Molecular and Cellular Biology, May 2004, pp. 4534-4545, vol. 24, No. 10.
Sharma, S. et al., "Development of Inhalational Agents for Oncologic Use," Journal of Clinical Oncology, Mar. 2001, Abstract, vol. 19, Issue 6.
Shen, H, et al., "A Novel Polymorphism in Human Cytosine DNA-Methyltransferase-3B Promoter is Associated with an Increased Risk of Lung Cancer," Cancer Research, Sep. 2002, pp. 4992-4995, vol. 62.

Takamizawa, J. et al., "Reduced Expression of the let-7 MicroRNAs in Human Lung Cancers in Association with Shortened Postoperative Survival," Cancer Research, Jun. 2004, pp. 3753-3756, vol. 64.

Tang, X. et al., "A Simple Array Platform for MicroRNA Analysis and its Application in Mouse Tissues," RNA, Aug. 2007, pp. 1-20, vol. 13.

Thomson, J. M. et al., "A Custom Microarray Platform for Analysis of MicroRNA Gene Expression," Nature Methods, Oct. 2004, pp. 1-7, vol. 1, No. 1.

Thorgeirsson, S. S. et al., "Functional Genomics of Hepatocellular Carcinoma," Hepatology, Feb. 2006, pp. S145-S150, vol. 43, No. 2, Suppl. 1.

Tockman, M. S. et al., "Considerations in Bringing a Cancer Biomarker to Clinical Application," Cancer Research, May 1992, pp. 2711s-2718s, vol. 52.

Trapasso, F. et al., "Fhit Interaction with Ferredoxin Reductase Triggers Generation of Reactive Oxygen Species and Apoptosis of Cancer Cells," Journal of Biological Chemistry, May 2008, pp. 13736-13744, vol. 283, No. 20.

Tricoli, J. V. et al., "MicroRNA: Potential for Cancer Detection, Diagnosis, and Prognosis," Cancer Research, May 2007, pp. 4553-4555, vol. 67, No. 10.

Ueda, T. et al., "Relation Between MicroRNA Expression and Progression and Prognosis of Gastric Cancer: A MicroRNA Expression Analysis," Published Online; www.thelancet.com/oncology, Dec. 2009, DOI:10.1016/S1470-2045(09)70343-2.

Valeri, N. et al., "Epigenetics, miRNAs, and Human Cancer: A New Chapter in Human Gene Regulation," Mamm Genome, Aug. 2009, pp. 573-580, vol. 20.

Varnholt, H. et al., "MicroRNA Gene Expression Profile of Hepatitis C Virus-Associated Hepatocellular Carcinoma," Hepatology, Apr. 2008, pp. 1223-1232, Vo. 47, No. 4.

Virgilio, L. et al., "Identification of the TCL1 Gene Involved in T-Call Malignancies," Proc. Natl. Acad. Sci., Dec. 1994, pp. 12530-12534, vol. 91.

Visone, R. et al., "MiRNAs and Cancer," The American Journal of Pathology, Apr. 2009, pp. 1131-1138, vol. 174, No. 4.

Volinia, et al., "Reprogramming of MirRNA Networks in Cancer and Leukemia," Genome Research, 2010, pp. 589-599, vol. 20.

Volinia, S. et al., "A MicroRNA Expression Signature of Human Solid Tumors Defines Cancer Gene Targets," PNAS, Feb. 2006, pp. 2257-2261, vol. 103, No. 7.

Wang, E. et al., "Ontogeny and Oncogenesis Balance the Transcriptional Profile of Renal Cell Cancer," Cancer Research, Oct. 2004, pp. 7279-7287, vol. 64.

Wang, X. et al., "Association Between CpG Island Methylation of the WWOX Gene and its Expression in Breast Cancers," Tumor Biology, Feb. 2009, pp. 8-14, vol. 30.

Weidhaas, J., "Using MicroRNAs to Understand Cancer Biology," Published Online Dec. 21, 2009, DOI: 10.1016/S1470-2045(09)70386-9.

Yamashita, T. et al., "Activation of Hepatic Stem Cell Marker EpCAM by Wnt-β-Catenin Signaling in Hepatocellular Carcinoma," Cancer Research, Nov. 2007, pp. 10831-10839, vol. 67, No. 22.

Yamashita, T. et al., "EpCAM and α-Fetoprotein Expression Defines Novel Prognostic Subtypes of Hepatocellular Carcinoma," Cancer Research, Mar. 2008, pp. 1451-1461, vol. 68, No. 5.

Yanaihara, N. et al., "Unique MicroRNA Molecular Profiles in Lung Cancer Diagnosis and Prognosis," Cancer Cell, Mar. 2006, pp. 189-198, vol. 9.

Yang, J. et al., "Analysis of Sequence Variations in 59 MicroRNAs in Hepatocellular Carcinomas," Mutation Research, Aug. 2008, pp. 205-209, vol. 638.

Yendamuri, S. et al., "WW Domain Containing Oxidoreductase Gene Expression is Altered in Non-Small Cell Lung Cancer," Cancer Research, Feb. 2003, pp. 878-881, vol. 63.

Yoon, S. et al., "Prediction of Regulatory Modules Comprising MicroRNAs and Target Genes," Bioinformatics Genes and Genomes, 2005. Pages ii93-ii100, vol. 21, Suppl. 2.

Yu, L.-G. et al., "Protein Phosphatase 2A, a Negative Regulator of the ERK Signaling Pathway, Is Activated by Tyrosine Phosphorylation of Putative HLA Class II—Associated Protein I (PHAPI)/pp32 in Response to the Antiproliferative Lectin, Jacalin," The Journal of Biological Chemisty, Jul. 2004, pp. 41377-41383, vol. 279, No. 40.

Zeng, Y. et al., "Recognition and Cleavage of Primary MicroRNA Precursors by the Nuclear Processing Enzyme Drosha," The EMBO Journal, 2005, pp. 138-148, vol. 24.

Zhang, L. et al., "Genomic and Epigenetic Alterations Deregulate MicroRNA Expression in Human Epithelial Ovarian Cancer," PNAS, May 2008, pp. 7004-7009, vol. 105, No. 19.

Zhang, L. et al., "MicroRNAs Exhibit High Frequency Genomic Alterations in Human Cancer," PNAS, Jun. 2006, pp. 9136-9141, vol. 103, No. 24.

Zhang, L. et al., Supporting Information, PNAS 2008, pp. 1-11.

Zhang, Z. et al., "Three Biomarkers Identified from Serum Proteomic Analysis for the Detection of Early Stage Ovarian Cancer," Cancer Research, Aug. 2004, pp. 5882-5890, vol. 64.

Zhu, S. et al., "MicroRNA-21 Targets the Tumor Suppressor Gene Tropomyosin 1 (TPM 1)," Journal of Biological Chemistry, May 2007, pp. 14328-14336, vol. 282, No. 19.

* cited by examiner

| Clinical Variable | Value[a] |
|---|---|
| Male | 213 (87) |
| Age at diagnosis--yr | |
|   Median | 50 |
|   Range | 13-83 |
| Viral Hepatitis Status[b] | |
|   CC | 172 (70) |
|   AVR-CC | 66 (27) |
|   No Data | 6 (2) |
| Tumor size--cm | |
|   ≤3 | 88 (36) |
|   >3 | 156 (64) |
| Multinodular | |
|   No | 191 (78) |
|   Yes | 53 (22) |
| Child-Pugh Class | |
|   A | 233 (96) |
|   B | 11 (4) |
| Metastasis/Recurrence | |
|   No | 146 (60) |
|   Yes | 98 (40) |
| TNM Stage | |
|   I | 99 (40) |
|   II | 90 (37) |
|   III | 53 (21) |
|   IV | 2 (<1) |

[a] Each value represents: the number of patients (the % of patients)
[b] CC, Chronic carrier; AVR-CC, active viral replication chronic carrier

Fig. 4 - Table 1

| Clinical variable | Survival | | | | | Recurrence | | | | |
|---|---|---|---|---|---|---|---|---|---|---|
| | Univariate analysis[a] | | Multivariate analysis[b] | | | Univariate analysis | | Multivariate analysis | | |
| | Hazard Ratio (95% CI)[c] | p value | Hazard Ratio (95% CI) | p value | | Hazard Ratio (95% CI) | p value | Hazard Ratio (95% CI) | p value | |
| miRNA predictor (M vs NM)[d] | 2.5 (1.1-5.8) | 0.027 | 3.0 (1.2-7.8) | 0.023 | | 2.9 (1.5-5.7) | 0.002 | 2.8 (1.4-5.7) | 0.004 | |
| Age (≥50yr vs <50yr) | 1.3 (0.6-2.8) | 0.463 | n.a.[f] | | | 1.4 (0.8-2.3) | 0.205 | n.a. | | |
| Sex (M vs F) | 1.8 (0.4-7.7) | 0.415 | n.a. | | | 1.4 (0.6-3.3) | 0.417 | n.a. | | |
| HBV (AVR-CC vs CC)[e] | 1.1 (0.5-2.5) | 0.726 | n.a. | | | 1.3 (0.8-2.2) | 0.276 | n.a. | | |
| AFP (>20ng/ml vs ≤20 ng/ml) | 1.3 (0.6-2.9) | 0.470 | 1.7 (0.7-3.8) | 0.215 | | 1.1 (0.6-1.8) | 0.825 | n.a. | | |
| Cirrhosis (Yes vs No) | 1.0 (0.2-4.1) | 0.961 | 1.3 (0.3-6.3) | 0.704 | | 1.4 (0.4-4.5) | 0.558 | n.a. | | |
| ALT (≥50U/L vs <50U/L) | 0.6 (0.3-1.4) | 0.257 | n.a. | | | 1.3 (0.8-2.1) | 0.296 | n.a. | | |
| Child-Pugh score (B vs A) | n.a. | n.a. | n.a. | | | n.a. | n.a. | n.a. | | |
| Tumor size (>3cm vs ≤3cm) | 3.3 (1.4-7.7) | 0.006 | 3.0 (1.2-7.4) | 0.015 | | 2.2 (1.3-3.6) | 0.002 | 1.9 (1.1-3.1) | 0.015 | |
| Tumor encapsulation (None vs Complete) | 1.1 (0.5-2.3) | 0.864 | n.a. | | | 0.6 (0.3-1.0) | 0.041 | n.a. | | |
| Multinodular (Yes vs No) | 0.2 (0.1-0.7) | 0.009 | 0.1 (0.0-0.5) | 0.003 | | 0.4 (0.2-0.7) | 0.003 | 0.3 (0.2-0.7) | 0.002 | |
| Microvascular invasion (Yes vs No) | 1.7 (0.8-3.7) | 0.146 | 0.7 (0.2-3.4) | 0.698 | | 1.1 (0.7-1.8) | 0.683 | n.a. | | |
| Edmondson Grade (III-IV vs I+II) | 1.0 (0.5-2.1) | 0.994 | n.a. | | | 1.2 (0.7-2.0) | 0.542 | n.a. | | |
| TNM stage (II vs I) | 1.2 (0.6-2.7) | 0.596 | 3.6 (0.7-18.6) | 0.127 | | 0.9 (0.5-1.4) | 0.587 | 1.7 (0.9-3.0) | 0.081 | |
| CLIP stage (1 vs 0) | 1.0 (0.5-2.2) | 0.993 | n.a. | | | 1.0 (0.6-1.7) | 0.920 | n.a. | | |
| CLIP stage (2 vs 0) | 0.5 (0.1-1.8) | 0.304 | n.a. | | | 0.4 (0.2-1.0) | 0.047 | n.a. | | |
| BCLC stage (B+C vs 0+A) | 0.7 (0.2-2.2) | 0.508 | n.a. | | | 1.1 (0.5-2.1) | 0.867 | n.a. | | |

[a] Univariate analysis, Cox proportional hazards regression
[b] Multivariate analysis, Cox proportional hazards regression
[c] 95% CI, 95% confidence interval
[d] miR predictor, predictor composed of 20 miRs
[e] CC, Chronic carrier; AVR-CC, active viral replication chronic carrier
[f] n.a.

Fig. 5 - Table 2

| No | miRNA | Genomic Location | Parametric p-value | % CV support | Mean Intensities in M | Mean Intensities in NM | Ratio (M/NM) | Expressed in metastatic HCC | Potential host targets* | Estimated false discovery rate (FDR)* |
|---|---|---|---|---|---|---|---|---|---|---|
| 1 | mir-219-1*** | 6q21.32 | 0.0002 | 100 | 578 | 391 | 1.48 | up | **PCDH17; **EPHA4 | 0.11; 0.14 |
| 2 | mir-207 | n.a. | 0.0002 | 90 | 3676 | 2432 | 1.51 | up | n.a. | |
| 3 | mir-338 | 17q25.3 | 0.0001 | 90 | 356 | 250 | 1.42 | up | n.a. | |
| 4 | mir-185 | 22q11.21 | 0.0009 | 40 | 461 | 346 | 1.33 | up | n.a. | |
| 5 | mir-30c-1 | 1p34.2 | 0.0001 | 90 | 813 | 1618 | 0.50 | down | KIAA0063 | 0.13 |
| 6 | mir-124a-2 | 8q12.3 | 0.0004 | 90 | 236 | 448 | 0.53 | down | G3BP2; GYS1; VAMP3 | 0.12; 0.14; 0.002 |
| 7 | mir-1-2 | 18q11.2 | 0.0002 | 80 | 294 | 571 | 0.51 | down | G3BP2; GCLC | 0.23; 0.15 |
| 8 | mir-19a | 13q31.3 | 0.0004 | 60 | 535 | 947 | 0.56 | down | n.a. | |
| 9 | mir-34a | 1p36.2 | 0.0005 | 50 | 261 | 539 | 0.48 | down | SPTBN2 | 0.3 |
| 10 | mir-9-2 | 5q14.3 | 0.0005 | 50 | 197 | 347 | 0.57 | down | RAB6A; SLC20A2; VAMP3 | 0.18; 0.077; 0.18 |
| 11 | mir-122a | 18q21.31 | 0.0002 | 50 | 466 | 781 | 0.60 | down | GYS1 | 0.12 |
| 12 | mir-148a | 7p15.2 | 0.0004 | 40 | 539 | 1084 | 0.50 | down | GTF2H1; PSCD3 | 0.27; 0.3 |
| 13 | mir-125b-2 | 21q21.1 | 0.0007 | 40 | 1346 | 2337 | 0.58 | down | ITGA9; YES1 | 0.25; 0.2 |
| 14 | mir-15a | 13q14.2 | 0.0010 | 40 | 294 | 461 | 0.64 | down | ASPH; SLC20A2; SPTBN2 | 0.26; 0.036; 0.24 |
| 15 | mir-30e | 1p34.2 | 0.0010 | 40 | 960 | 1512 | 0.63 | down | n.a. | |
| 16 | mir-148b | 12q13.13 | 0.0005 | 30 | 578 | 1063 | 0.54 | down | GTF2H1; PSCD3; **CSF1 | 0.27; 0.23; 0.24 |
| 17 | mir-194 | 1q41 | 0.0008 | 30 | 406 | 689 | 0.59 | down | HBEGF | 0.15 |
| 18 | mir-30a | 6q13 | 0.0008 | 30 | 2915 | 4572 | 0.64 | down | n.a. | |
| 19 | mir-126 | 9q34.3 | 0.0009 | 30 | 226 | 395 | 0.57 | down | n.a. | |
| 20 | let-7g | 3p21.2 | 0.0009 | 30 | 582 | 838 | 0.69 | down | PSCD3 | 0.14 |

*Potential host target genes with estimated FDR are based on TARGETSCAN. These genes are a part of the 153-gene metastasis signature described in Ye et al, Nat Med, 9, 416-423, 2003, except the three genes marked with ** that are associated with HCC venous metastases recently identified (Budhu et al, Cancer Cell 2006, 10(2):99-111).

***The 4-miRNA predictor consists of miR-219-1, miR-207, miR-30c-1 and miR-124a-2.

Fig. 6 - Table 3

| Clinical Variable | Value[a] |
|---|---|
| BCLC Staging | |
| 0 | 6 (5) |
| A | 74 (67) |
| B | 27 (25) |
| C | 3 (3) |
| CLIP Staging | |
| 0 | 45 (41) |
| 1 | 40 (36) |
| 2 | 25 (23) |
| OKUDA Staging | |
| 0 | 99 (90) |
| 1 | 11 (10) |
| TNM Staging | |
| I | 32 (29) |
| II | 56 (51) |
| III | 22 (19) |

[a] Each value represents: the number of patients (the % of patients)

Fig. 7 - Table 4

Fig. 8 - Table 5

| Clinical variable | Survival | | | | Recurrence | | | |
|---|---|---|---|---|---|---|---|---|
| | Univariate analysis[a] | | Multivariate analysis[b] | | Univariate analysis | | Multivariate analysis | |
| | Hazard Ratio (95% CI)[c] | p value | Hazard Ratio (95% CI) | p value | Hazard Ratio (95% CI) | p value | Hazard Ratio (95% CI) | p value |
| miR predictor (M vs NM)[d] | 2.5 (1.1-6.2) | 0.033 | 3.4 (1.3-9.0) | 0.012 | 3.0 (1.4-6.4) | 0.004 | 2.9 (1.3-6.3) | 0.009 |
| Age (≥50yr vs <50yr) | 1.5 (0.7-3.2) | 0.330 | n.a.[f] | | 1.3 (0.7-2.2) | 0.387 | n.a.[f] | |
| Sex (M vs F) | 1.4 (0.3-5.9) | 0.653 | n.a. | | 1.6 (0.6-4.3) | 0.398 | n.a. | |
| HBV (AVR-CC vs CC)[e] | 1.4 (0.6-3.1) | 0.393 | n.a. | | 1.3 (0.8-2.2) | 0.356 | n.a. | |
| AFP (>20ng/ml vs ≤20 ng/ml) | 1.4 (0.6-3.2) | 0.365 | 1.7 (0.8-3.9) | 0.190 | 1.0 (0.6-1.7) | 0.953 | n.a. | |
| Cirrhosis (Yes vs No) | 0.8 (0.2-3.4) | 0.753 | n.a. | | 2.0 (0.5-8.4) | 0.321 | n.a. | |
| ALT (≥50U/L vs <50U/L) | 0.9 (0.4-2.0) | 0.818 | n.a. | | 1.3 (0.8-2.2) | 0.324 | n.a. | |
| Child-Pugh score (B vs A) | n.a. | n.a. | n.a. | | n.a. | n.a. | n.a. | |
| Tumor size (>3cm vs ≤3cm) | 3.6 (1.5-8.5) | 0.004 | 4.0 (1.6-10.2) | 0.004 | 2.9 (1.6-4.9) | 0.000 | 1.8 (1.0-3.3) | 0.044 |
| Tumor encapsulation (None vs Complete) | 1.1 (0.5-2.5) | 0.750 | n.a. | | 0.6 (0.4-1.1) | 0.118 | n.a. | |
| Multinodular (Yes vs No)[g] | n.a. | n.a. | n.a. | | 0.3 (0.1-0.6) | 0.001 | 0.3 (0.1-0.7) | 0.007 |
| Microvascular invasion (Yes vs No) | 1.8 (0.8-4.0) | 0.136 | 2.3 (0.3-19.2) | 0.450 | 1.1 (0.7-1.9) | 0.662 | n.a. | |
| Edmondson Grade (III+IV vs I+II) | 1.0 (0.5-2.2) | 0.998 | n.a. | | 1.1 (0.6-1.9) | 0.786 | n.a. | |
| TNM stage (II vs I) | 1.3 (0.6-2.9) | 0.561 | 1.0 (0.1-10.0) | 0.970 | 0.9 (0.5-1.5) | 0.667 | 1.8 (1.0-3.2) | 0.970 |
| TNM stage (III vs I) | 1.0 (0.1-7.6) | 0.974 | 0.4 (0.0-8.1) | 0.555 | n.a. | n.a. | n.a. | |
| CLIP stage (1 vs 0) | 1.0 (0.4-2.1) | 0.925 | n.a. | | 1.0 (0.6-1.8) | 0.988 | n.a. | |
| CLIP stage (2 vs 0) | 0.3 (0.0-2.4) | 0.258 | n.a. | | 0.3 (0.0-1.0) | 0.042 | n.a. | |
| BCLC stage (A vs 0) | 2.2 (0.3-16.3) | 0.438 | n.a. | | 1.4 (0.5-3.8) | 0.550 | n.a. | |
| Okuda stage (1 vs 0) | 1.2 (0.4-3.6) | 0.706 | n.a. | | 0.8 (0.3-2.1) | 0.722 | n.a. | |

[a] Univariate analysis, Cox proportional hazards regression
[b] Multivariate analysis, Cox proportional hazards regression
[c] 95% CI, 95% confidence interval
[d] miR predictor, predictor composed of 20 miRs
[e] CC, Chronic carrier; AVR-CC, active viral replication chronic carrier
[f] n.a., not applicable

| Clinical variable | Survival | | | | Recurrence | | | |
|---|---|---|---|---|---|---|---|---|
| | Univariate analysis[a] | | Multivariate analysis[b] | | Univariate analysis | | Multivariate analysis | |
| | Hazard Ratio (95% CI)[c] | p value | Hazard Ratio (95% CI) | p value | Hazard Ratio (95% CI) | p value | Hazard Ratio (95% CI) | p value |
| miRNA predictor (M vs NM)[d] | 2.7 (1.3-5.8) | 0.009 | 3.3 (1.5-7.4) | 0.003 | 1.9 (1.0-3.5) | 0.057 | 2.3 (1.2-4.6) | 0.013 |
| Age (≥50yr vs <50yr) | 1.3 (0.7-2.6) | 0.452 | n.a.[f] | | 1.4 (0.9-2.3) | 0.122 | n.a. | |
| Sex (M vs F) | 1.7 (0.4-7.0) | 0.486 | n.a. | | 1.2 (0.5-2.8) | 0.672 | n.a. | |
| HBV (AVR-CC vs CC)[e] | 1.5 (0.7-3.0) | 0.250 | n.a. | | 1.3 (0.8-2.2) | 0.234 | n.a. | |
| AFP (>20ng/ml vs ≤20 ng/ml) | 1.3 (0.6-2.8) | 0.478 | n.a. | | 1.0 (0.6-1.7) | 0.956 | n.a. | |
| Cirrhosis (Yes vs No) | 1.3 (0.5-3.6) | 0.669 | n.a. | | 1.9 (0.6-6.0) | 0.280 | n.a. | |
| ALT (≥50U/L vs <50U/L) | 0.8 (0.4-1.6) | 0.503 | n.a. | | 1.1 (0.7-1.8) | 0.561 | n.a. | |
| Child-Pugh score (B vs A) | n.a. | n.a. | n.a. | | n.a. | n.a. | n.a. | |
| Tumor size (>3cm vs ≤3cm) | 2.7 (1.2-6.2) | 0.021 | 2.8 (1.2-6.7) | 0.017 | 1.5 (0.9-2.4) | 0.117 | n.a. | |
| Tumor encapsulation (None vs Complete) | 1.2 (0.6-2.5) | 0.648 | n.a. | | 0.7 (0.4-1.2) | 0.205 | n.a. | |
| Multinodular (Yes vs No) | 0.3 (0.1-0.7) | 0.006 | 0.2 (0.1-0.6) | 0.002 | 0.3 (0.2-0.5) | <0.001 | 0.2 (0.1-0.4) | <0.001 |
| Microvascular invasion (Yes vs No) | 1.9 (0.9-3.9) | 0.075 | n.a. | | 1.1 (0.7-1.8) | 0.562 | n.a. | |
| Edmondson Grade (III+IV vs I+II) | 1.1 (0.5-2.1) | 0.948 | n.a. | | 1.2 (0.7-1.9) | 0.564 | n.a. | |
| TNM stage (II vs I) | 1.2 (0.6-2.7) | 0.588 | 3.1 (1.3-7.2) | 0.010 | 0.9 (0.5-1.4) | 0.567 | 1.7 (1.0-3.1) | 0.053 |
| TNM stage (III vs I) | 0.7 (0.2-2.2) | 0.519 | 1.6 (0.4-5.8) | 0.506 | 0.3 (0.1-0.8) | 0.010 | 0.6 (0.2-1.7) | 0.309 |
| CLIP stage (1 vs 0) | 1.0 (0.6-2.7) | 0.602 | n.a. | | 0.8 (0.5-1.3) | 0.410 | n.a. | |
| CLIP stage (2 vs 0) | 0.7 (0.2-2.3) | 0.544 | n.a. | | 0.4 (0.2-0.7) | 0.006 | n.a. | |
| BCLC stage (B+C vs 0+A) | 0.6 (0.2-1.4) | 0.242 | n.a. | | 0.5 (0.3-0.9) | 0.028 | 2.2 (0.9-5.7) | 0.097 |
| Okuda stage (1 vs 0) | 1.7 (0.7-4.1) | 0.236 | n.a. | | 1.3 (0.6-2.7) | 0.506 | 2.0 (0.9-4.6) | 0.085 |

[a] Univariate analysis, Cox proportional hazards regression
[b] Multivariate analysis, Cox proportional hazards regression
[c] 95% CI, 95% confidence interval
[d] mR predictor, predictor composed of 20 mRs
[e] CC, Chronic carrier; AVR-CC, active viral replication chronic carrier
[f] n.a., not applicable

Fig. 9 - Table 6

| SEQ ID NO | microRNA | Sequence (5'-...-3') |
|---|---|---|
| 1 | miR-126 | UCGUACCGUGAGUAAUAAUGCG |
| 2 | miR-122 | UGGAGUGUGACAAUGGUGUUUG |
| 3 | miR-148b | UCAGUGCAUCACAGAACUUUGU |
| 4 | miR-124a | UAAGGCACGCGGUGAAUGCC |
| 5 | miR-194 | UGUAACAGCAACUCCAUGUGGA |
| 6 | miR-30c | UGUAAACAUCCUACACUCUCAGC |
| 7 | miR-30a | UGUAAACAUCCUCGACUGGAAG |
| 8 | miR-148a | UCAGUGCACUACAGAACUUUGU |
| 9 | miR-30e | UGUAAACAUCCUUGACUGGAAG |
| 10 | miR-34a | UGGCAGUGUCUUAGCUGGUUGU |
| 11 | Let-7g | UGAGGUAGUAGUUUGUACAGUU |
| 12 | miR-125b | UCCCUGAGACCCUAACUUGUGA |
| 13 | miR-1 | UGGAAUGUAAAGAAGUAUGUAU |
| 14 | miR-19a | UGUGCAAAUCUAUGCAAAACUGA |
| 15 | miR-15a | UAGCAGCACAUAAUGGUUUGUG |
| 16 | miR-9 | UCUUUGGUUAUCUAGCUGUAUGA |
| 17 | miR-185 | UGGAGAGAAAGGCAGUUCCUGA |
| 18 | miR-207 | GCUUCUCCUGGCUCUCCUCCCUC |
| 19 | miR-219-5p | UGAUUGUCCAAACGCAAUUCU |
| 20 | miR-219-3p | AGAGUUGAGUCUGGACGUCCCG |
| 21 | miR-338-5p | AACAAUAUCCUGGUGCUGAGUG |
| 22 | miR-338-3p | UCCAGCAUCAGUGAUUUUGUUG |

MICRORNA EXPRESSION SIGNATURE FOR PREDICTING SURVIVAL AND METASTASES IN HEPATOCELLULAR CARCINOMA

CROSS-REFERENCE TO RELATED APPLICATIONS

This application claims the benefit of PCT application No. PCT/US07/023660 filed Nov. 1, 2007 which claims priority to U.S. Provisional Application No. 60/855,895, filed Nov. 1, 2006, the disclosures of which are incorporated herein by reference.

STATEMENT REGARDING SPONSORED RESEARCH

This invention was made with government support under NCI Grant No. RO1 CA128609. The government has certain rights in this invention.

BACKGROUND OF THE INVENTION

Hepatocellular carcinoma (HCC) represents an extremely poor prognostic cancer that remains one of the most common and aggressive human malignancies worldwide (1; 2). The dismal outcome has been attributed to the major hallmarks of HCC, intra-hepatic metastases or post-surgical recurrence. New tumor colonies frequently invade into the major branches of the portal vein and possibly other parts of the liver (3-6). Resection or liver transplantation, are the best options for a potential cure however, only about 20 percent of HCC patients, defined by parameters of relatively normal liver function and a manageable tumor lesion as determined by the available clinical staging systems, are currently eligible for surgical intervention. Moreover, resected patients often have a high frequency of metastasis/recurrence, and post-operative 5 year survival is only 30-40 percent.

Liver transplantation for HCC patients remains controversial due to a shortage of organ donors and the poor performance of current staging systems in selecting appropriate candidates, especially at early disease stages. These systems are essential, particularly in malignant diseases, to provide advice to patients and guidance for assessment and treatment. Clinical evaluation and therapeutic decisions in HCC is complex because they depend on both the grade of cancer spread (tumor staging) and residual liver function (chronic liver disease stage). Although well-defined and generally accepted staging systems are available for almost all cancers, HCC is an exception, with many different staging systems globally introduced to accommodate each stratum of the disease and a current lack of consensus on which one is best (7-12). Thus, an accurate prognostic predictor and a sensible selection criterion that can be applied to HCC patients for rational treatment decisions remains a challenging task.

The recent identification of prognostic molecular biomarkers offers hope for advance diagnosis of HCC. Using cDNA microarray technology, the inventors developed a unique gene expression signature to predict prognosis and metastasis of HCC patients (13). The presence of a molecular prognostic signature in primary HCC clinical specimens was confirmed by several recent studies (14; 15). Since HCC is usually present in inflamed liver, the inventors also developed a unique predictor based on the expression of genes in the liver microenvironment of HCC patients, which was principally different from that of the tumor (16). Like many other prognostic signatures based on cDNA gene expression profiling, both the tumor and microenvironment signatures contain several hundred cellular coding genes. Therefore, it would be a challenging task to identify relevant biomarkers or potential pharmacological targets and interrogate scores of genes in clinical practice.

Recent studies indicate that expression profiling with small non-coding RNA gene products (~22 nt) known as microRNAs (miRNAs or miRs) is a superior method for cancer subtype classification and prognostication (17-19). miRNAs exist in many organisms and play key regulatory roles in mRNA translation and degradation by base pairing to partially complementary sites of the mRNA, predominantly in the 3' untranslated region (20-22). miRNAs are expressed as long precursor RNAs that are processed by Drosha, a cellular nuclease, and subsequently transported to the cytoplasm by an Exportin-5-dependent mechanism (23; 24). miRNAs are then cleaved by the DICER enzyme, resulting in—17-24 nt miRNAs that associate with a RNA-induced silencing-like complex (25; 26). The expression patterns, function and regulation of miRNAs in normal and neoplastic human cells are largely unknown but emerging data and their frequent location at fragile sites, common break-points or regions of amplification or loss of heterozygosity reveal that they may play significant roles in human carcinogenesis.

The enhanced expression of precursor miR-155 in Burkitt's lymphomas and the frequent deletion or downregulation of several miRNAs have been observed in B cell chronic lymphocytic leukemia (CLL) and in many cancer types, including breast, lung, ovarian, cervical, colorectal, prostate, and lymphoid (17; 18; 27-34). Functional analysis has also revealed the downregulation of PTEN by miR-21, the tumor suppressor function of the let-7 family and the oncogenic function of the miR17-92 cluster (35-37). The biological and clinical relevance of miRNA expression patterns have been shown in human B cell CLL and solid tumors, including breast cancers (18; 30; 38). Each miRNA has the unique capability to potentially regulate the expression of hundreds of coding genes and thereby modulate several cellular pathways including proliferation, apoptosis and stress response (39). This phenomenon makes miRNAs superior molecular markers and targets for interrogation and as such, miRNA expression profiling can be utilized as a tool for cancer diagnosis (17; 40).

SUMMARY OF THE INVENTION

In a broad aspect, there is provided herein a unique miRNA signature that can significantly distinguish HCC venous metastasis from metastasis-free HCC. In contrast to HCC staging systems, this signature is capable of predicting survival and recurrence of HCC patients with multinodular or solitary tumors, including those with early-stage disease. Moreover, this signature is an independent and significant predictor of patient prognosis and relapse when compared to other available clinical parameters. This miRNA signature is useful to enable HCC prognosis and has clinical utility for the advance identification of HCC patients with a propensity towards metastasis/recurrence.

There is provided herein a system of the identification of a chronic hepatocellular carcinoma (HCC), cancer-specific signature of miRNAs that are differentially expressed relative to normal control cells.

Accordingly, provided herein are methods of diagnosing whether a subject has, or is at risk for developing, HCC comprising measuring the level of at least one miR gene product in a test sample from the subject, wherein an alteration in the level of the miR gene product in the test sample, relative to the level of a corresponding miR gene product in a control sample, is indicative of the subject either having, or being at risk for developing, HCC.

The level of the at least one miR gene product can be measured using a variety of techniques that are well-known to those of skill in the art. In one embodiment, the level of the at least one miR gene product is measured using Northern blot analysis. In another embodiment, the level of the at least one miR gene product in the test sample is less than the level of the corresponding miR gene product in the control sample. Also, in another embodiment, the level of the at least one miR gene product in the test sample can be greater than the level of the corresponding miR gene product in the control sample.

Also provided herein are methods of diagnosing a HCC associated with one or more prognostic markers in a subject, comprising measuring the level of at least one miR gene product in a HCC sample from the subject, wherein an alteration in the level of the at least one miR gene product in the test sample, relative to the level of a corresponding miR gene product in a control sample, is indicative of the subject having a HCC associated with the one or more prognostic markers.

In one embodiment, the level of the at least one miR gene product is measured by reverse transcribing RNA from a test sample obtained from the subject to provide a set of target oligodeoxynucleotides; hybridizing the target oligodeoxynucleotides to a microarray comprising miRNA-specific probe oligonucleotides to provide a hybridization profile for the test sample; and, comparing the test sample hybridization profile to a hybridization profile generated from a control sample. An alteration in the signal of at least one miRNA is indicative of the subject either having, or being at risk for developing, HCC.

Also provided herein are methods of treating HCC in a subject, wherein the signal of at least one miRNA, relative to the signal generated from the control sample, is de-regulated (e.g., down-regulated and/or up-regulated).

In certain embodiments, a microarray comprises miRNA-specific probe oligonucleotides for one or more miRNAs selected from one or more of the SEQ ID NOS: 1-22, as shown in FIG. 11, and, in particular certain embodiments, one miR gene product comprises one or more of: miR-219 [SEQ ID NO: 20], miR-207 [SEQ ID NO: 18], miR-30c [SEQ ID NO: 6], and miR124A [SEQ ID NO: 4].

Also provided herein are methods of diagnosing whether a subject has, or is at risk for developing, a HCC associated with one or more adverse prognostic markers in a subject, by reverse transcribing RNA from a test sample obtained from the subject to provide a set of target oligodeoxynucleotides; hybridizing the target oligodeoxynucleotides to a microarray comprising miRNA-specific probe oligonucleotides to provide a hybridization profile for the test sample; and, comparing the test sample hybridization profile to a hybridization profile generated from a control sample. An alteration in the signal is indicative of the subject either having, or being at risk for developing, the cancer.

Also provided herein are methods of treating HCC in a subject who has HCC in which at least one miR gene product is down-regulated or up-regulated in the cancer cells of the subject relative to control cells. When the one or more miR gene product is down-regulated in the cancer cells, the method comprises administering to the subject an effective amount of at least one isolated miR gene product, such that proliferation of cancer cells in the subject is inhibited. When one or more miR gene product is up-regulated in the cancer cells, the method comprises administering to the subject an effective amount of at least one compound for inhibiting expression of at least one miR gene product, such that proliferation of cancer cells in the subject is inhibited. In certain embodiments, the at least one isolated miR gene product is selected miR-219 [SEQ ID NO: 20], miR-207 [SEQ ID NO: 18], miR-30c [SEQ ID NO: 6] and miR124A and combinations thereof.

Also provided herein are methods of treating HCC in a subject, comprising: determining the amount of at least one miR gene product in HCC cells, relative to control cells; and, altering the amount of miR gene product expressed in the HCC cells by: administering to the subject an effective amount of at least one isolated miR gene product, if the amount of the miR gene product expressed in the cancer cells is less than the amount of the miR gene product expressed in control cells; or administering to the subject an effective amount of at least one compound for inhibiting expression of the at least one miR gene product, if the amount of the miR gene product expressed in the cancer cells is greater than the amount of the miR gene product expressed in control cells, such that proliferation of cancer cells in the subject is inhibited. In certain embodiments, at least one isolated miR gene product is selected from the group consisting of miR-219 [SEQ ID NO: 20], miR-207 [SEQ ID NO: 18], miR-30c [SEQ ID NO: 6] and miR124A, and combinations thereof.

Also provided herein are pharmaceutical compositions for treating HCC, comprising at least one isolated miR gene product and a pharmaceutically-acceptable carrier. In a particular embodiment, the pharmaceutical compositions comprise at least one isolated miR gene product corresponds to a miR gene product that is down-regulated in HCC cells relative to suitable control cells.

In another particular embodiment, the pharmaceutical composition comprises at least one miR expression regulator (for example, an inhibitor) compound and a pharmaceutically-acceptable carrier.

Also provided herein are pharmaceutical compositions that include at least one miR expression regulator compound that is specific for a miR gene product that is up- or down-regulated in HCC cells relative to suitable control cells.

Also provided herein are methods of identifying an anti-HCC agent, comprising providing a test agent to a cell and measuring the level of at least one miR gene product associated with decreased expression levels in HCC cells, wherein an increase in the level of the miR gene product in the cell, relative to a suitable control cell, is indicative of the test agent being an anti-HCC agent. In certain embodiments, the miR gene product comprises one or more of the SEQ ID NOS: 1-22, as shown in FIG. 11. In particular certain embodiments, one miR gene product comprises one or more of: miR-219 [SEQ ID NO: 20], miR-207 [SEQ ID NO: 18], miR-30c [SEQ ID NO: 6], and miR124A [SEQ ID NO: 4].

Also provided herein are methods of identifying an anti-HCC agent, comprising providing a test agent to a cell and measuring the level of at least one miR gene product associated with increased expression levels in HCC cells, wherein a decrease in the level of the miR gene product in the cell, relative to a suitable control cell, is indicative of the test agent being an anti-HCC agent.

In certain embodiments, the miR gene product comprises one or more of the SEQ ID NOS: 1-22, as shown in FIG. 11. In particular certain embodiments, one miR gene product comprises one or more of: miR-219 [SEQ ID NO: 20], miR-207 [SEQ ID NO: 18], miR-30c [SEQ ID NO: 6], and miR124A [SEQ ID NO: 4].

Various objects and advantages of this invention will become apparent to those skilled in the art from the following detailed description of the preferred embodiment, when read in light of the accompanying drawings.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 2: Significant differentially expressed miRNAs in metastatic vs non-metastatic liver tissues from HCC patients.

FIG. 4. Table 1 showing the clinical characteristics of patients for Example I.

FIG. 5. Table 2 showing univariate and multivariate analyses of factors associated with survival and recurrences (TMM stage I and II).

FIG. 6. Table 3—Summary of 20 micro RNAs with a prognostic value to predict HCC survival/

FIG. 7. Table 4—Clinical staging of the poorly-defined set.

FIG. 8. Table 5—Univariate and multivariate analyses of factors associated with survival and recurrence (BCLC Stage 0 and A).

FIG. 9. Table 6—Univariate and multivariate analyses of factors associated with survival and recurrence.

FIG. 11. A table containing a set of 22 miRNAs useful for predicting HCC, [SEQ ID NOS: 1-22].

DETAILED DESCRIPTION OF THE PREFERRED EMBODIMENT

Figure 1:
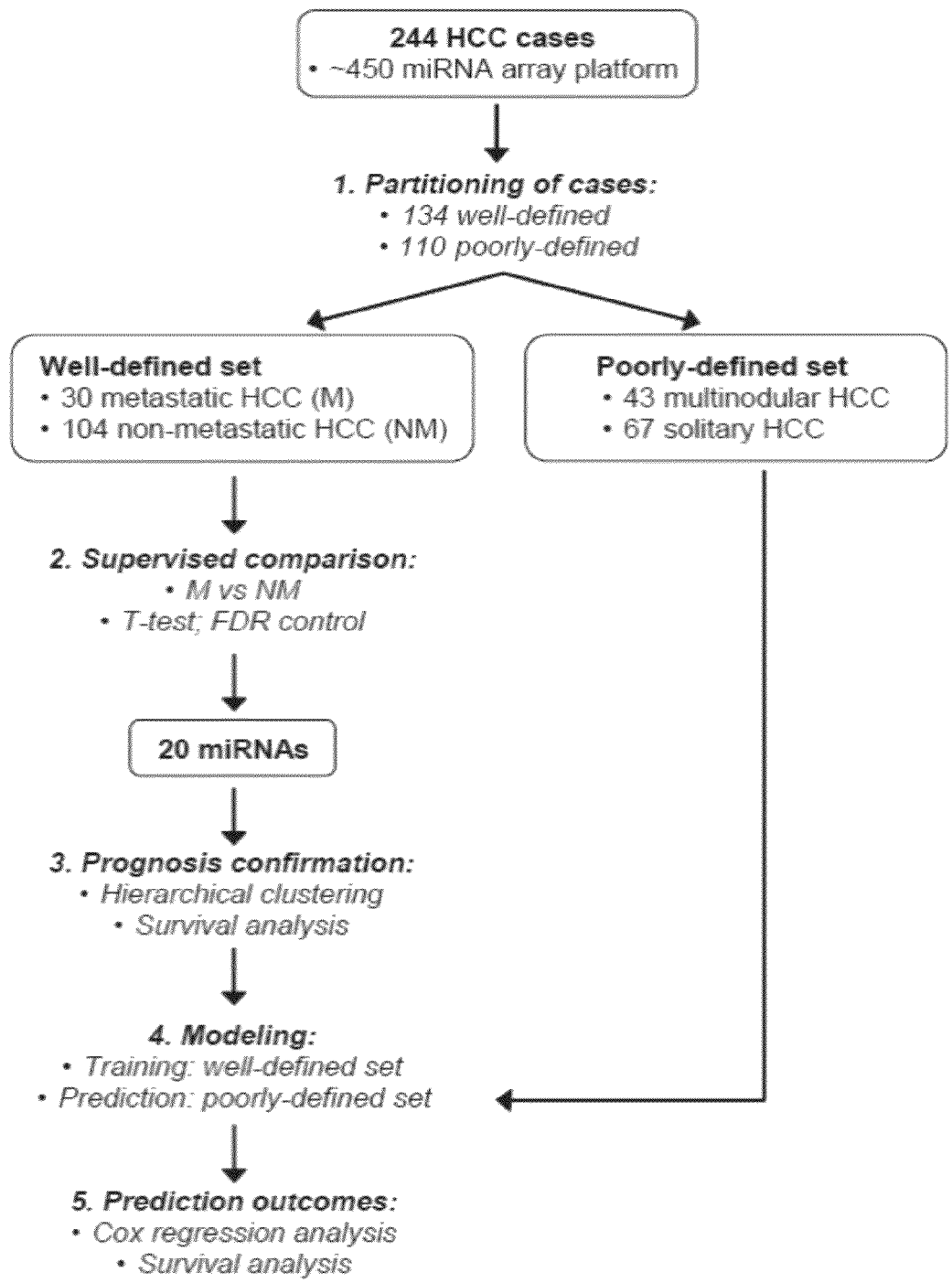
FIG. 1: Schematic of the search for a miRNA signature that can predict HCC prognosis.

It is to be understood that both the foregoing general description and the following detailed description are exemplary and explanatory only and are not intended to limit the scope of the current teachings. In this application, the use of the singular includes the plural unless specifically stated otherwise.

The use of the word "a" or "an" when used in conjunction with the term "comprising" in the claims and/or the specification may mean "one," but it is also consistent with the meaning of "one or more," "at least one," and "one or more than one."

Also, the use of "comprise", "contain", and "include", or modifications of those root words, for example but not limited to, "comprises", "contained", and "including", are not intended to be limiting. The term "and/or" means that the terms before and after can be taken together or separately. For illustration purposes, but not as a limitation, "X and/or Y" can mean "X" or "Y" or "X and Y".

It is understood that an miRNA is derived from genomic sequences or a gene. In this respect, the term "gene" is used for simplicity to refer to the genomic sequence encoding the precursor miRNA for a given miRNA. However, embodiments of the invention may involve genomic sequences of a miRNA that are involved in its expression, such as a promoter or other regulatory sequences.

The term "miRNA" generally refers to a single-stranded molecule, but in specific embodiments, molecules implemented in the invention will also encompass a region or an additional strand that is partially (between 10 and 50% complementary across length of strand), substantially (greater than 50% but less than 100% complementary across length of strand) or fully complementary to another region of the same single-stranded molecule or to another nucleic acid. Thus, nucleic acids may encompass a molecule that comprises one or more complementary or self-complementary strand(s) or "complement(s)" of a particular sequence comprising a molecule. For example, precursor miRNA may have a self-complementary region, which is up to 100% complementary miRNA probes of the invention can be or be at least 60, 65, 70, 75, 80, 85, 90, 95, or 100% complementary to their target.

The term "combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, ACB, CBA, BCA, BAC, or CAB.

The section headings used herein are for organizational purposes only and are not to be construed as limiting the described subject matter in any way. All literature and similar materials cited in this application, including patents, patent applications, articles, books, treatises, and interne web pages are expressly incorporated by reference in their entirety for any purpose. In the event that one or more of the incorporated literature and similar materials defines or uses a term in such a way that it contradicts that term's definition in this application, this application controls.

MicroRNAs (miRNAs) are transcripts of a new class of small noncoding RNA genes that are able to distinguish several types of aggressive cancers, including hepatocellular carcinoma (HCC), from their normal counterparts. HCC patients have a very poor prognosis due to high rate of metastasis, and current staging systems are not capable of accurately determining patient prognosis, especially at early stages of this disease. The inventors investigated whether unique miRNAs are associated with prognosis and metastases in HCC.

The inventors examined the miRNA expression profiles of 490 specimens from radical resection of 244 HCC patients.

The inventors discovered a unique miRNA signature based on 134 clinically well-defined metastatic and non-metastatic HCC specimens. The unique signature was used to predict the prognostic outcomes of a 110 independent HCC specimens.

The miRNA signature composed of 20 unique oligonucleotides can significantly discriminate (p<0.001) 30 primary HCC tissues with venous metastases from 104 metastasis-free solitary HCC with cross validation in a training cohort. However, significant miRNAs could not be identified from the corresponding non-cancerous hepatic tissues.

The tumor metastasis miRNA signature was a significant predictor of patient survival (p<0.0023) and recurrence (p=0.002) is 89 early stage HCC. A refined signature composed of 4 selected miRNAs had a similar prediction power. Notably, high miR-219 [SEQ ID NO: 20] and miR-207 [SEQ ID NO: 18] and low miR-30c [SEQ ID NO: 6] and miR-124a [SEQ ID NO: 4] expression correlated with venous metastases and poor survival. Cox proportional hazards modeling also revealed that this signature was superior to other clinical variables, including the known staging systems, for predicting patient survival.

The unique miRNA signature is useful for HCC prognosis, particularly in patients whose outcome is hard to predict by conventional staging systems. The examples herein show that measurement of certain miRNA levels in HCC have clinical utility for the advance identification of patients who are likely to develop metastases and subsequently classify them for appropriate treatment.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example I

HCC and Associated Conditions

Hepatic tissues were obtained with informed consent from patients who underwent radical resection between 2002 and 2003 at the Liver Cancer Institute and Zhongshan Hospital (Fudan University, Shanghai, China). The study was approved by the Institutional Review Board of the Liver Cancer Institute and NIH. Gene expression profiles were conducted in primary HCC and corresponding noncancerous hepatic tissues from 244 Chinese HCC patients. Among them, 93% had underlying cirrhosis and 68% had a serum alpha-fetoprotein (AFP) level >20 ng/ml (FIG. 4-Table 1).

The general strategy for partitioning cases and testing the miRNA signature is outlined in FIG. 1. A total of 134 well-defined cases were used as the training group. Among them, 30 had primary HCC lesions accompanied by tumor emboli found in the major branches of the portal vein (n=25), inferior vena cava (n=2) or common bile duct (n=4; one also with tumor thrombi in inferior vena cava) and 104 had solitary HCC with no metastasis/recurrence found at follow-up (3 yr).

In the validation analysis, the inventors used a testing group of 110 independent cases (FIG. 1: poorly-defined set) whose prognosis could not be accurately determined at the time of resection by several HCC staging systems. The testing cases included 43 multinodular and 67 solitary HCC. Of the 43 multinodular HCC cases, 18 developed intrahepatic recurrence and one developed extrahepatic metastasis in addition to an intrahepatic recurrence. Of the 67 solitary HCC cases, 4 patients had a solitary tumor with an appearance of aggregated nodules, 10 developed intra- and/or extrahepatic metastases while 49 developed intrahepatic recurrence confirmed at follow-up (3 yr). In addition, eight normal liver tissues from disease-free patients [described in (16)] were included as normal controls.

RNA Isolation and miRNA Arrays:

The RNA isolation and miRNA array methodology were essentially as previously described (13; 17). In the analysis of the 244 HCC cases, RNA was isolated in a pairwise fashion from tumor or non-tumor tissue and samples were selected in random order for miRNA analysis to avoid grouping bias. A total of 488 microarrays were performed (see Example II).

Statistical Analyses:

Unsupervised hierarchical clustering analysis was performed by the GENESIS software version 1.5 developed by Alexander Sturn (IBMT-TUG, Graz, Austria). The BRB ArrayTools software V3.3 was used for supervised analysis, as previously described (13; 16). The Kaplan-Meier survival analysis was used to compare patient survival based on prediction results, using Excel-based WinSTAT software. The statistical p value was generated by the Cox-Mantel log-rank test. Cox proportional hazards regression was used to analyze the effect of sixteen clinical variables on patient survival or recurrence using STATA 9.2 (College Station, Tex.) (see Example II). The statistical significance was defined as p<0.05. TargetScan analysis was based on a website tool developed by Ben Lewis (see Example II) (41).

Results:

The Search for a miRNA Metastasis Signature in HCC Tissues.

Figure 2A:
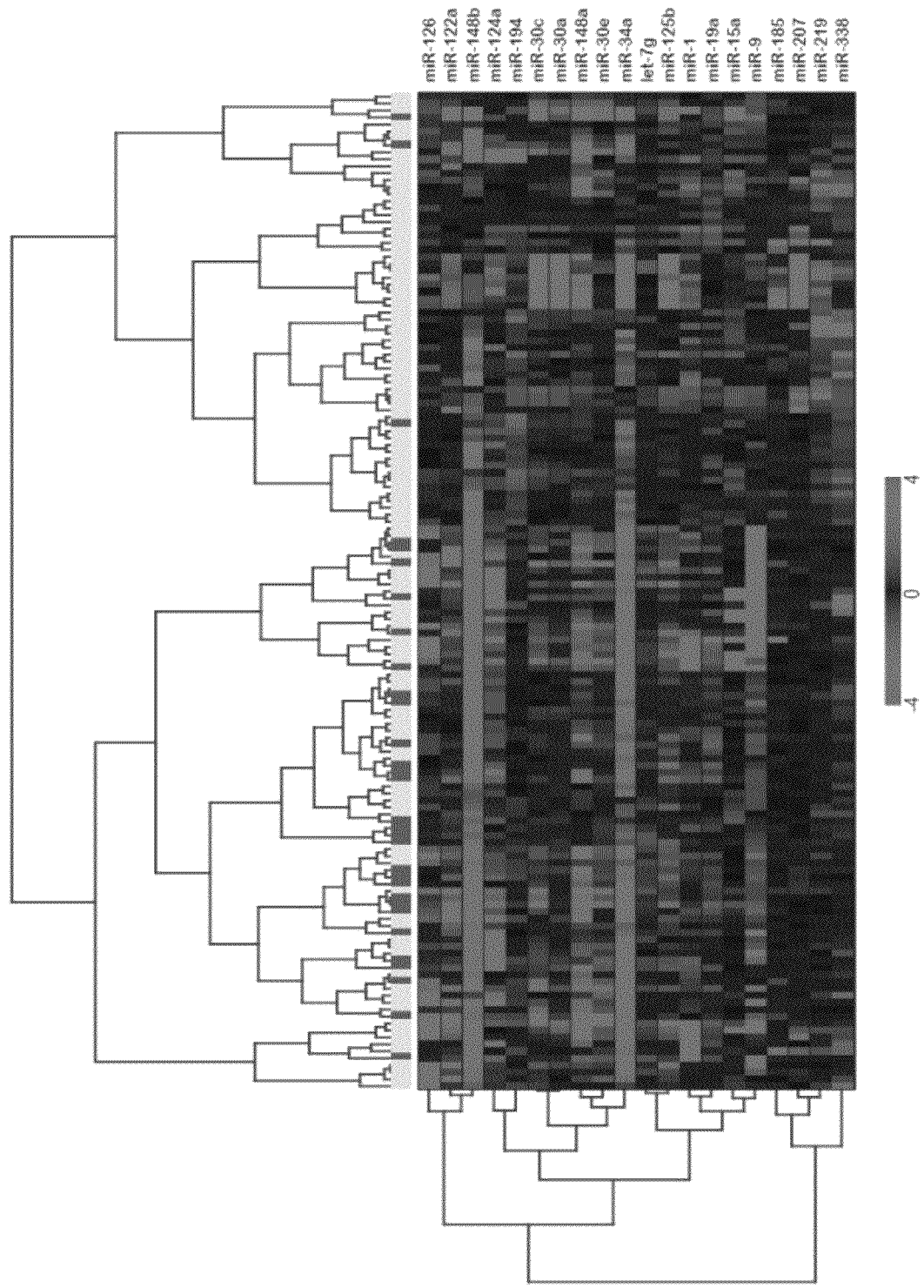
(FIG. 2A) Hierarchical clustering of 20 miRNA genes whose expression was significantly (p<0.001) altered in metastasis (M; blue bars; n=30) and non-metastasis samples (NM; yellow bars; n=104) from class prediction analysis using 4 different algorithms (compound covariate predictor, linear discriminant analysis, nearest neighbor and support vector machines) employing leave-one-out cross validation to establish prediction accuracy. Each row represents an individual gene and each column represents an individual tissue sample. Genes were ordered by center correlation and complete linkage according to the ratios of abundance in each tissue sample compared to a normal liver tissue pool (n=8), which were normalized to the mean abundance of genes. Pseudocolors indicate transcript levels below, equal, or above the mean (green, black and red, respectively). The scale represents the gene expression ratios from −4 to 4 in log 2 scale.

In a cohort of 244 HCC cases, the inventors compared primary HCC or noncancerous tissues from 30 cases with venous metastases (M) and 104 non-metastasis cases (NM) by a supervised class comparison approach (see methods in Example II) (FIG. 1, and FIG. 4-Table 1). The inventors identified 20 miRNAs that can discriminate the tumor tissues of M from NM cases (FIG. 2A and FIG. 6-Table 3).

When the non-cancerous tissue miRNA expression data were used, the inventors could not identify any miRNA capable of distinguishing M from NM at the same statistical significance level (data not shown). Thus, there are more measurable changes in miRNA expression in tumor cells compared to that of the hepatic microenvironment, which suggests that analysis of miRNA expression in tumor tissues may be better suited for differentiating HCC patient groups.

Moreover, significant miRNAs could not be identified when a comparison of these tissues was made with other clinical variables including multinodular status, microvascular invasion and 4 clinical staging systems (data not shown). Therefore, the expression of certain miRNAs appeared to correlate with metastasis only when macrovascular invasion was evident. Of the 20 miRNAs, 4 were overexpressed in M while 16 were overexpressed in NM.

Composition and Predictive Value of a Refined miRNA Metastasis Signature.

Figure 2B:
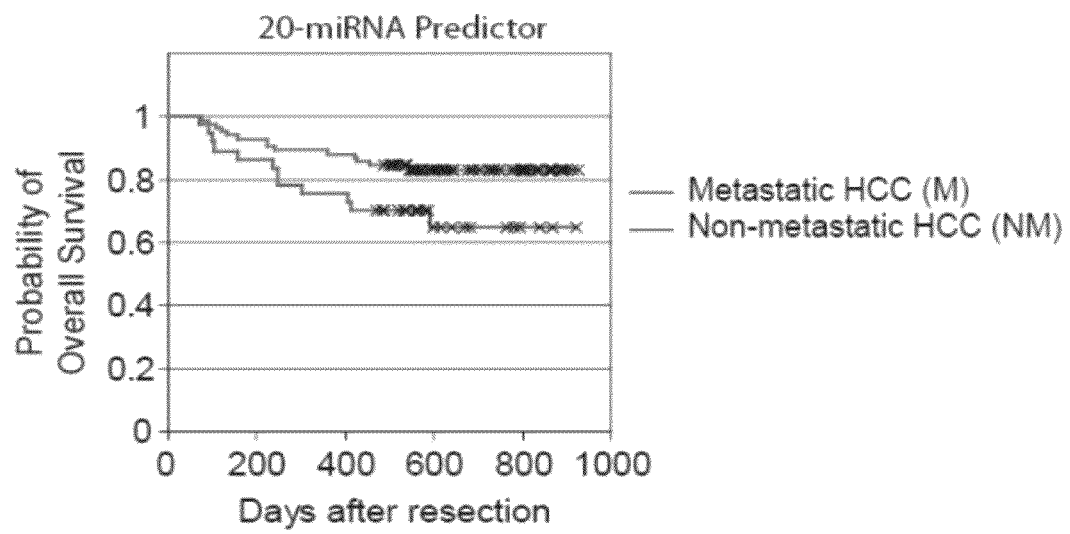
(FIG. 2B) Kaplan-Meier survival analysis of metastasis and non-metastasis samples based on prediction outcome of the 20 miRNAs.

To determine if the 20-miRNA signature was related to patient prognosis, the inventors first performed multivariate nearest neighbor class prediction with 10% cross-validation and 1000 permutations. This analysis resulted in a statistically significant prediction of metastases with an overall accuracy of 76% (p=0.001). Kaplan Meier survival analysis based on the 20-miRNA prediction results revealed that the predicted metastasis group had a significantly shorter survival period when compared to the non-metastasis group (p<0.042) (FIG. 2B). Thus, this signature is associated with patient prognosis.

Figure 3A:
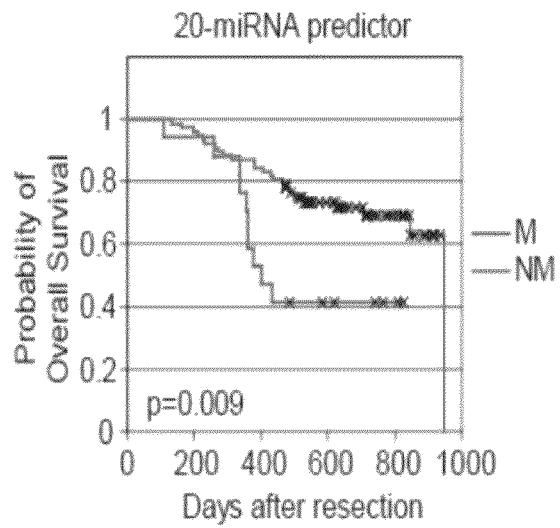
FIG. 3: Analysis of the classification capacity of the 20-miRNA or 4-miRNA signature in the testing cohort or early-stage HCC. Kaplan-Meier overall survival analysis of 110 HCC patients based on predicted classification by the (FIG. 3A) 20-miRNA predictor.
(FIG. 3B) 4-miRNA predictor. Kaplan-Meier overall survival analysis of 89 early-stage HCC patients based on predicted classification by the (FIG. 3C) 20-miRNA predictor (FIG. 3D) 4-miRNA predictor. Kaplan-Meier relapse-free survival analysis of 89 early-stage HCC patients based on predicted classification by the (FIG. 3E) 20-miRNA predictor (FIG. 3F) 4-miRNA predictor.

To further test the robustness of the miRNA signature, the inventors tested its ability to predict an independent set of HCC cases based on the results of the cross-validated training set (FIG. 1). The inventors found that the predicted M group had a significantly worse survival rate than the NM group (p=0.009) (FIG. 3A).

Figure 3B:
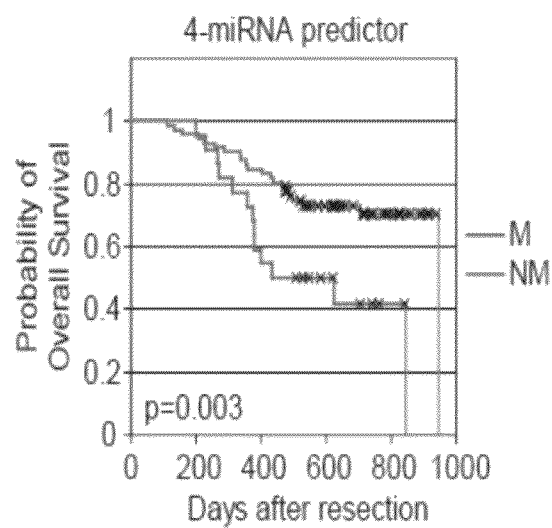

Using a gene reduction approach with various miRNA combinations, the inventors found that significant prediction of survival can still be achieved with only 4 miRNAs miR-219 [SEQ ID NO: 20], miR-207 [SEQ ID NO: 18], miR-30c [SEQ ID NO: 6], and miR124A [SEQ ID NO: 4] (p=0.003) (FIG. 3B).

It appeared that an increased expression of miR-219 [SEQ ID NO: 20] and miR-207 [SEQ ID NO: 18] and decreased expression of miR-30c [SEQ ID NO: 6] and miR-124a [SEQ ID NO: 4] are associated with HCC venous metastases and prognosis (FIG. 6-Table 3).

In contrast, 4 HCC prognostic staging systems (i.e., TNM, OKUDA, CLIP or BCLC) were incapable of predicting patient survival in this testing cohort (FIG. 6-FIG. 3, FIG. 7-Table 4, and FIG. 8-Table 5).

Figure 3C:
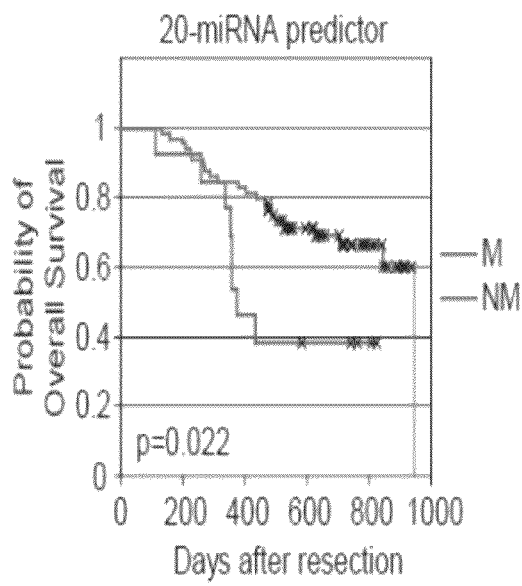
Figure 3D:
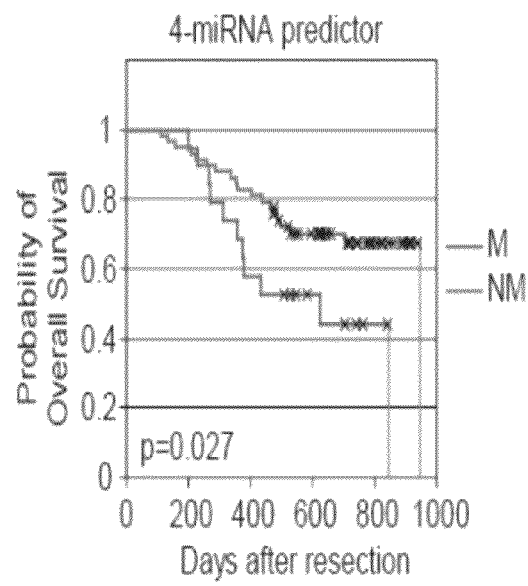

Since the ability to predict risk of cancer spread at early stages of HCC can have a significant clinical impact, the inventors also assayed the prognostic capacity of the 20- or 4miRNA signature for early stage HCC patients (TNM stage I or II; n=89). Similar to the entire testing set, a significantly worse survival was observed for the predicted M patients versus NM by both the 20- or 4-miRNA signature in the early stage cohort (p=0.022 or p=0.027) (FIGS. 3C and D).

Figure 3E:
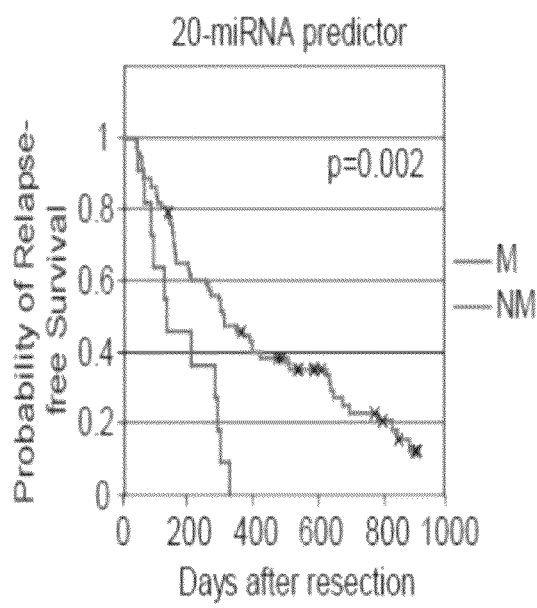
Figure 3F:
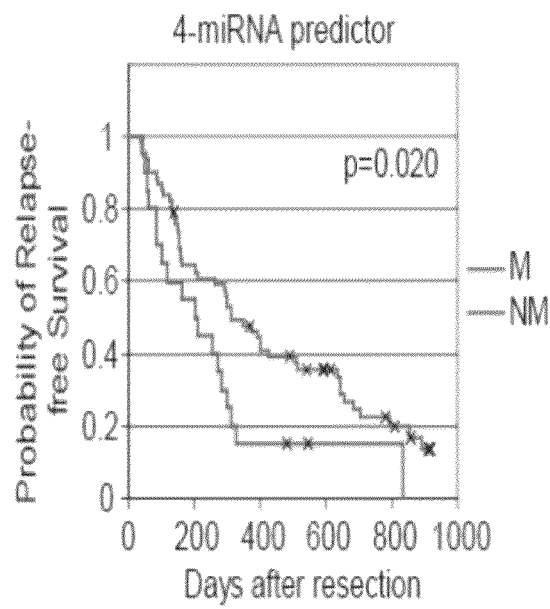
Figure 10A:
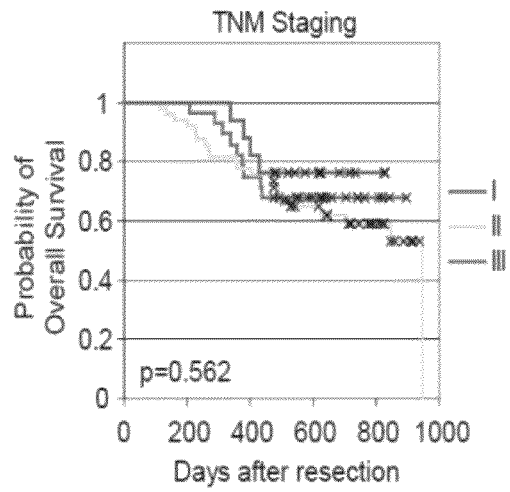
FIG. 10. Analysis of the classification capacity of staging systems in the testing cohort. Kaplan-Meier survival analysis of 110 HCC patients based on predicted classification by (FIG. 10A) TNM staging (FIG. 10B) OKUDA staging (FIG. 10C) CLIP staging or (FIG. 10D) BCLC staging.
Figure 10B:
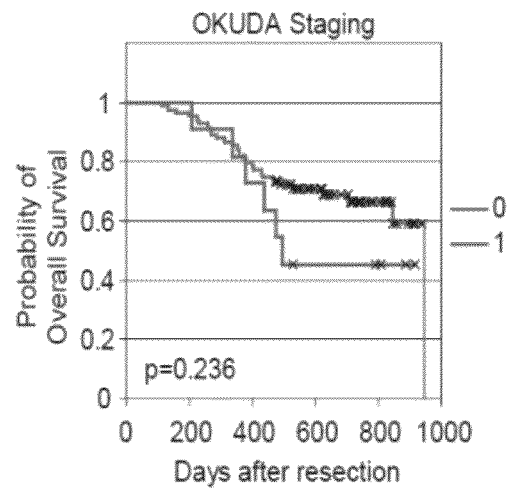
Figure 10C:
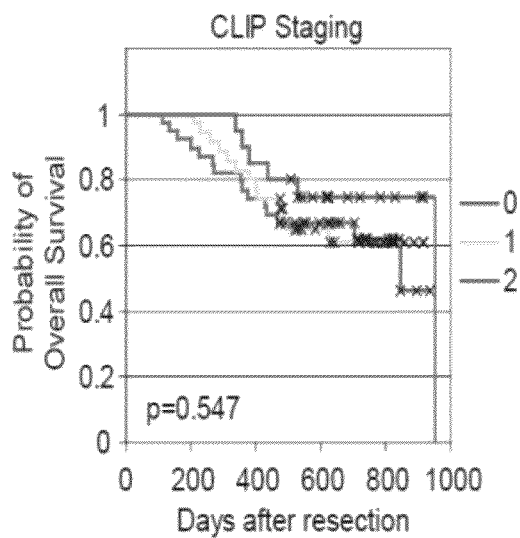
Figure 10D:
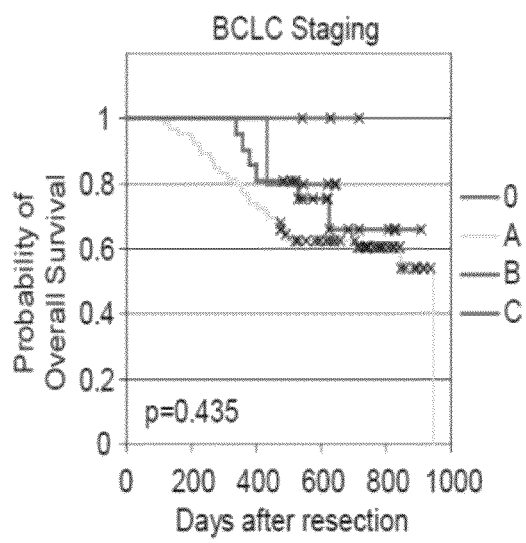

In addition, the inventors also tested the capacity of the signatures to predict recurrence in the early stage cohort and found that the predicted M group based on the 20 or 4 miRNA signature had a higher recurrence rate (p=0.002 or p=0.020) than the NM group (FIGS. 3E and F, FIG. 5-Table 2).

Meanwhile, the clinical staging systems were incapable of predicting overall or disease-free survival in this cohort (FIG. 5-Table 2). Thus, the miRNA signature identified is a superior predictor of HCC patient outcome, particularly for early stage disease.

Comparison of the miRNA Predictor and Known Clinical Staging Systems.

Next, the inventors performed Cox proportional hazards regression analysis to determine whether the miRNA predictor was confounded by underlying clinical conditions within the early stage cohort. A univariate analysis revealed that the miRNA signature was a significant predictor of survival and recurrence (p=0.027 and p=0.002, respectively) (FIG. 5-Table 2).

The multivariate parsimonious survival model, which controlled for potential confounding covariates demonstrated that the miRNA predictor was associated with a significant 3.0 fold increased risk of death for patients with the M versus the NM expression profile (FIG. 5-Table 2).

The multivariate parsimonious recurrence model, demonstrated that the miRNA predictor was associated with a significant 2.8 fold increased risk of recurrence for those with the M expression profile compared with that of NM (FIG. 5-Table 2) when controlling for potential confounders. The inventors also performed Cox regression analysis on an early stage cohort determined by BCLC staging (Stage 0 and A) and on the entire testing cohort and found similar results (FIG. 8 Table 5 and FIG. 9-Table 6).

In contrast, the clinical HCC staging systems were not capable of predicting patient prognosis and relapse within the testing cohort (FIG. 5-Table 2 and FIG. 8-Table 5). Thus, the miRNA signature is an independent predictor for both survival and relapse.

Discussion of Example I

A majority of HCC patients are diagnosed at a late stage and only a small percentage fit resection or transplantation criteria. The outcome of HCC patients has been less than satisfactory, largely due to the lack of a simple, validated and universal clinical staging system with robust predictive power, especially for early stage patients and for those with solitary or multinodular HCC that eventually metastasize or recur. Thus, a key challenge to improving HCC patient outcome is early detection and classification.

The inventors have shown that the expression of 20 miRNAs, or even 4 miRNAs, can significantly predict the survival of HCC patients with solitary or multinodular tumors who develop metastasis/recurrence and can effectively do so in HCC patients with relatively small tumors who were at an early stage of this disease. In contrast, the clinical HCC staging systems were unable to distinguish the outcome of these patients.

The 4 miRNAs with the most significant weight in the signature have not been associated with the progression of any human malignancies reported and may therefore be uniquely associated with metastatic HCC. The inventors note that since multinodular HCC patients had a better survival and recurrence rate than solitary HCC patients within this cohort, the association of these outcomes was inversely associated with nodular type.

Isolation, amplification and expression analysis techniques for miRNA are rapidly progressing, increasing the likelihood of feasible miRNA profiling in clinical tissue. Since miRNAs can be used to provide a higher accuracy in subtype classification and the examples herein show a superior ability to distinguish classically poor-to-predict HCC patient cohorts, grouping patients according to their miRNA signature expression may have clinical utility. The advance identification of poor prognosis patients (M) by the miRNA signature may allow for more personalized, directed or aggressive treatment regimens than patients classified in the good prognosis group (NM).

The miRNAs and/or the miRNA signature may also be used for prioritizing HCC patients to receive liver transplantation because of the limited supply of available donors and the lack of an adequate allocation system.

Another advantage is that, for optimum clinical use and potentially more efficient diagnosis, it would be appropriate to have a minimum number of genes that can discriminate patients who are likely to develop more aggressive forms of the disease. The inventors have demonstrated that as few as 4 miRNAs are capable of significantly discriminating HCC patients who have a poor outcome. Thus, these miRNAs are promising tools that may facilitate HCC diagnosis, particularly for early stage patients, and allow for appropriate clinical counsel and treatment.

The miRNAs and/or Mir signature can be also useful to identify candidate miRNA targets that are differentially expressed in patients who develop metastases/recurrence.

Also, these miRNAs are useful to provide insight into the biological consequence of miRNA alteration in HCC. The miRNAs and/or miR signature is also useful to develop and/or serve as therapeutic targets to reverse the potential outcome of patients with a poor prognostic signature defined by miRNA classification.

Another advantage is the miRNAs and/or miR signature is useful in developing methods and/or compositions to reverse the course of the disease. Such reversion possibilities may occur, for example, through gene therapy options to alter the expression of miRNAs or their targets. Other non-limiting examples include inactivation of oncogenic phenotypes by synthetic antisense oligonucleotides, generation of specific inhibitors to abrogate miRNA/target gene interaction or overexpression of tumor suppressive phenotypes using viral or liposomal delivery.

The miRNAs and/or miR signature are useful for the early diagnosis and associated interventional treatment and can be used to change the rather fatalistic approach to HCC. The miRNA signature disclosed herein can thus be used to classify HCC patients at an early stage, enabling their diagnosis and improving clinical outcome.

Example II

HBV and Associated Hepatic Conditions

The sample enrollment criteria included those with a history of hepatitis B virus HBV infection or HBV-related liver cirrhosis, HCC diagnosed by two independent pathologists, detailed information on clinical presentation and pathological characteristics; and detailed follow-up data for at least 3 years, which included intrahepatic recurrence, intrahepatic venous metastasis, lymph node involvement, extrahepatic metastases, disease-free and overall survival, as well as the cause of death.

The updated TNM classification is superior to other staging systems, including CLIP and Okuda for HCC patients who undergo resection and was therefore chosen to stratify early stage patients (TNM stage I and II) for analysis of miRNA prediction capacity (1; 2). Since a prospective study revealed that the BCLC system was superior to the new TNM classification system updated in 2002, the inventors also performed Cox proportional hazards modeling based on early stage patients categorized by BCLC (Stage 0 and A).

miRNA Arrays:

The miRNA microarray platform (V 2.0) was composed of 250 non-redundant human and 200 mouse miRNAs and arrays were performed at the Microarray Shared Resource, Comprehensive Cancer Center at the Ohio State University. To examine the robustness of the miRNA array platform, the inventors first analyzed whether miRNA expression can differentiate 244 HCC tissues from their paired surrounding noncancerous hepatic tissues (FIG. 4-Table 6).

Using a supervised class comparison method with a univariate paired t-test and a multivariate test with 1000 permutations of the class label with the false discovery rate set to <1 with 99% confidence, the inventors identified 209 non-redundant miRNAs that can significantly discriminate HCC tumor tissues (T) from their paired nontumor tissue (NT) (data not shown)

These significant miRNAs clearly separate T and NT samples, illustrated by hierarchical clustering analysis (data not shown). Multivariate class prediction algorithm analyses with 10% cross-validation and 100 random permutations indicated that these miRNAs can provide a statistically significant prediction of T and NT samples (p<0.01) with a >97% accuracy by the nearest neighbor predictor (data not shown). These initial analyses indicated that the miRNA arrays were robust and can identify a significant difference between tumor and noncancerous hepatic tissues. The same method was used to compare metastasis (M) and non-metastasis (NM) cases.

Statistical Analyses:

Cox proportional hazards regression was used to analyze the effect of clinical variables on patient overall and relapse-free survival, including age, sex, HBV active status, pre-resection alphafetoprotein (AFP), cirrhosis, alanine transferase (ALT), Child-Pugh score, tumor size, tumor encapsulation, nodular type, the status of microvascular invasion, Edmondson grade and several HCC prognosis staging systems including BCLC staging (3), CLIP classification (4), Okuda staging (5), or TNM classification (AJCC/UICC, 6th edition) (6). A univariate test was used to examine the influence of the miRNA predictor or each clinical variable on patient survival or recurrence for the entire testing set (n=110; FIG. 8-Table 5 and FIG. 9-Table 6) or early stage HCC (n=89; FIG. 5-Table 2).

A multivariate analysis was performed to estimate the hazards ratio of the miRNA predictor while controlling for clinical variables identified from a stepwise selection process using both forward addition and backwards selection routines with significance set at p<0.05. Furthermore, the hazards ratio for the miRNA predictor alone was compared to the hazards ratio for the miRNA predictor with each of the clinical variables. If a 10% change in the hazards ratio of the predictor was observed with the addition of a single covariate, this variable was controlled for in the final Cox proportional hazards model.

For the entire testing set, the most parsimonious survival model included the 20 miRNA predictor, tumor size, multinodular status and TNM staging while the most parsimonious recurrence model included the 20 miRNA predictor, multinodular status, TNM staging, BCLC staging and Okuda staging. For the early stage HCC set, the most parsimonious survival model included the 20 miRNA predictor, AFP, cirrhosis, tumor size, multinodular status, microvascular invasion and TNM staging while the most parsimonious recurrence model included the 20 miRNA predictor, tumor size, multinodular status and TNM staging.

Multi-collinearity of the covariates was assessed and was not found to be present and it was determined that all final models met the proportional hazards assumption. The statistical significance was defined as p<0.05. The inventors do note that in the univariate analyses Child-Pugh class could not be accurately analyzed due to the small sample size within this covariate compared to the other assessed clinical variables in this cohort.

To provide a sense of confidence in the potential miRNA target list output generated from the TargetScan bioinformatics approach, the inventors restricted the search by focusing on potential miRNA targets that were part of the 153-gene HCC tumor signature of venous metastases identified recently (7) and had a low FDR score (<0.3).

The inventors further limited output to only those potential cellular targets whose expression in metastatic HCC was inversely correlated with that of the corresponding miRNA. A summary of these host targets based on the search criteria described above is included in FIG. 6-Table 3.

FIG. 10 shows an analysis of the classification capacity of staging systems in the testing cohort. Kaplan-Meier survival analysis of 110 HCC patients based on predicted classification by (A) TNM staging (B) OKUDA staging (C) CLIP staging or (D) BCLC staging.

Example III

In one particular aspect, there is provided herein a method of diagnosing whether a subject has, or is at risk for developing, hepatocellular carcinoma (HCC). The method generally includes measuring the level of at least one miR gene product in a test sample from the subject and determining whether an alteration in the level of the miR gene product in the test sample, relative to the level of a corresponding miR gene product in a control sample, is indicative of the subject either having, or being at risk for developing, HCC. In certain embodiments, the level of the at least one miR gene product is measured using Northern blot analysis. Also, in certain embodiments, the level of the at least one miR gene product in the test sample is less than the level of the corresponding miR gene product in the control sample, and/or the level of the at least one miR gene product in the test sample is greater than the level of the corresponding miR gene product in the control sample.

In certain embodiments, the miR gene product comprises one or more of the SEQ ID NOS: 1-22, as shown in FIG. 11. In particular certain embodiments, one miR gene product comprises one or more of: miR-219 [SEQ ID NO: 20], miR-207 [SEQ ID NO: 18], miR-30c [SEQ ID NO: 6], and miR124A [SEQ ID NO: 4].

Example IV

Measuring miR Gene Products

The level of the at least one miR gene product can be measured by reverse transcribing RNA from a test sample obtained from the subject to provide a set of target oligodeoxynucleotides; hybridizing the target oligodeoxynucleotides to a microarray comprising miRNA-specific probe oligonucleotides to provide a hybridization profile for the test sample; and, comparing the test sample hybridization profile to a hybridization profile generated from a control sample. An alteration in the signal of at least one miRNA is indicative of the subject either having, or being at risk for developing, HCC.

Example V

Diagnostic and Therapeutic Applications

In another aspect, there is provided herein are methods of treating HCC in a subject, where the signal of at least one miRNA, relative to the signal generated from the control sample, is de-regulated (e.g., down-regulated and/or up-regulated).

In certain embodiments, the miR gene product comprises one or more of the SEQ ID NOS: 1-22, as shown in FIG. 11. In particular certain embodiments, one miR gene product comprises one or more of: miR-219 [SEQ ID NO: 20], miR-207 [SEQ ID NO: 18], miR-30c [SEQ ID NO: 6], and miR124A [SEQ ID NO: 4] and combinations thereof.

Also provided herein are methods of diagnosing whether a subject has, or is at risk for developing, a HCC associated with one or more adverse prognostic markers in a subject, by reverse transcribing RNA from a test sample obtained from the subject to provide a set of target oligodeoxynucleotides; hybridizing the target oligodeoxynucleotides to a microarray comprising miRNA-specific probe oligonucleotides to provide a hybridization profile for the test sample; and, comparing the test sample hybridization profile to a hybridization profile generated from a control sample. An alteration in the signal is indicative of the subject either having, or being at risk for developing, the cancer.

Also provided herein are methods of treating HCC in a subject who has HCC in which at least one miR gene product is down-regulated or up-regulated in the cancer cells of the subject relative to control cells. When the one or more miR gene product is down-regulated in the cancer cells, the method comprises administering to the subject an effective amount of at least one isolated miR gene product, such that proliferation of cancer cells in the subject is inhibited. When one or more miR gene product is up-regulated in the cancer cells, the method comprises administering to the subject an effective amount of at least one compound for inhibiting expression of at least one miR gene product, such that proliferation of cancer cells in the subject is inhibited. In certain embodiments, the at least one isolated miR gene product is selected miR-219 [SEQ ID NO: 20], miR-207 [SEQ ID NO: 18], miR-30c [SEQ ID NO: 6] and miR124A and combinations thereof.

Also provided herein are methods of treating HCC in a subject, comprising: determining the amount of at least one miR gene product in HCC cells, relative to control cells; and, altering the amount of miR gene product expressed in the HCC cells by: administering to the subject an effective amount of at least one isolated miR gene product, if the amount of the miR gene product expressed in the cancer cells is less than the amount of the miR gene product expressed in control cells; or administering to the subject an effective amount of at least one compound for inhibiting expression of the at least one miR gene product, if the amount of the miR gene product expressed in the cancer cells is greater than the amount of the miR gene product expressed in control cells, such that proliferation of cancer cells in the subject is inhibited. In certain embodiments, the miR gene product comprises one or more of the SEQ ID NOS: 1-22, as shown in FIG. 11. In particular certain embodiments, one miR gene product comprises one or more of: miR-219 [SEQ ID NO: 20], miR-207 [SEQ ID NO: 18], miR-30c [SEQ ID NO: 6], and miR124A [SEQ ID NO: 4] and combinations thereof.

Example VI

Compositions

Also provided herein are pharmaceutical compositions for treating HCC, comprising at least one isolated miR gene product and a pharmaceutically-acceptable carrier. In a particular embodiment, the pharmaceutical compositions comprise at least one isolated miR gene product corresponds to a miR gene product that is down-regulated in HCC cells relative to suitable control cells. In certain embodiments, the miR gene product comprises one or more of the SEQ ID NOS: 1-22, as shown in FIG. 11. In particular certain embodiments, one miR gene product comprises one or more of: miR-219 [SEQ ID NO: 20], miR-207 [SEQ ID NO: 18], miR-30c [SEQ ID NO: 6], and miR124A [SEQ ID NO: 4].

In another particular embodiment, the pharmaceutical composition comprises at least one miR expression regulator (for example, an inhibitor) compound and a pharmaceutically-acceptable carrier.

Also provided herein are pharmaceutical compositions that include at least one miR expression regulator compound that is specific for a miR gene product that is up- or down-regulated in HCC cells relative to suitable control cells.

Also provided herein are methods of identifying an anti-HCC agent, comprising providing a test agent to a cell and measuring the level of at least one miR gene product associated with decreased expression levels in HCC cells, wherein an increase in the level of the miR gene product in the cell, relative to a suitable control cell, is indicative of the test agent being an anti-HCC agent. In certain embodiments, the miR gene product comprises one or more of the SEQ ID NOS:

1-22, as shown in FIG. 11. In particular certain embodiments, one miR gene product comprises one or more of: miR-219 [SEQ ID NO: 20], miR-207 [SEQ ID NO: 18], miR-30c [SEQ ID NO: 6], and miR124A [SEQ ID NO: 4] and combinations thereof.

Also provided herein are methods of identifying an anti-HCC agent, comprising providing a test agent to a cell and measuring the level of at least one miR gene product associated with increased expression levels in HCC cells, wherein a decrease in the level of the miR gene product in the cell, relative to a suitable control cell, is indicative of the test agent being an anti-HCC agent. In a particular embodiment, the miR gene product is selected from the group consisting of miR-219 [SEQ ID NO: 20], miR-207 [SEQ ID NO: 18], miR-30c [SEQ ID NO: 6] and miR124A and combinations thereof.

Example VII

Kits

Any of the compositions described herein may be comprised in a kit. In a non-limiting example, reagents for isolating miRNA, labeling miRNA, and/or evaluating an miRNA population using an array are included in a kit. The kit may further include reagents for creating or synthesizing miRNA probes. The kits will thus comprise, in suitable container means, an enzyme for labeling the miRNA by incorporating labeled nucleotide or unlabeled nucleotides that are subsequently labeled. It may also include one or more buffers, such as reaction buffer, labeling buffer, washing buffer, or a hybridization buffer, compounds for preparing the miRNA probes, and components for isolating miRNA. Other kits may include components for making a nucleic acid array comprising oligonucleotides complementary to miRNAs, and thus, may include, for example, a solid support.

For any kit embodiment, including an array, there can be nucleic acid molecules that contain a sequence that is identical or complementary to all or part of any of SEQ ID NOS: 1-22.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit (labeling reagent and label may be packaged together), the kit also will generally contain a second, third or other additional container into which the additional components may be separately placed. However, various combinations of components may be comprised in a vial. The kits of the present invention also will typically include a means for containing the nucleic acids, and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being one preferred solution. Other solutions that may be included in a kit are those solutions involved in isolating and/or enriching miRNA from a mixed sample.

However, the components of the kit may be provided as dried powder(s). When reagents and/or components are provided as a dry powder, the powder can be reconstituted by the addition of a suitable solvent. It is envisioned that the solvent may also be provided in another container means. The kits may also include components that facilitate isolation of the labeled miRNA. It may also include components that preserve or maintain the miRNA or that protect against its degradation. The components may be RNAse-free or protect against RNAses.

Also, the kits can generally comprise, in suitable means, distinct containers for each individual reagent or solution. The kit can also include instructions for employing the kit components as well the use of any other reagent not included in the kit. Instructions may include variations that can be implemented. It is contemplated that such reagents are embodiments of kits of the invention. Also, the kits are not limited to the particular items identified above and may include any reagent used for the manipulation or characterization of miRNA.

It is also contemplated that any embodiment discussed in the context of an miRNA array may be employed more generally in screening or profiling methods or kits of the invention. In other words, any embodiments describing what may be included in a particular array can be practiced in the context of miRNA profiling more generally and need not involve an array per se.

It is also contemplated that any kit, array or other detection technique or tool, or any method can involve profiling for any of these miRNAs. Also, it is contemplated that any embodiment discussed in the context of an miRNA array can be implemented with or without the array format in methods of the invention; in other words, any miRNA in an miRNA array may be screened or evaluated in any method of the invention according to any techniques known to those of skill in the art. The array format is not required for the screening and diagnostic methods to be implemented.

The kits for using miRNA arrays for therapeutic, prognostic, or diagnostic applications and such uses are contemplated by the inventors herein. The kits can include an miRNA array, as well as information regarding a standard or normalized miRNA profile for the miRNAs on the array. Also, in certain embodiments, control RNA or DNA can be included in the kit. The control RNA can be miRNA that can be used as a positive control for labeling and/or array analysis.

The methods and kits of the current teachings have been described broadly and generically herein. Each of the narrower species and sub-generic groupings falling within the generic disclosure also form part of the current teachings. This includes the generic description of the current teachings with a proviso or negative limitation removing any subject matter from the genus, regardless of whether or not the excised material is specifically recited herein.

Example VIII

Array Preparation and Screening

Also provided herein are the preparation and use of miRNA arrays, which are ordered macroarrays or microarrays of nucleic acid molecules (probes) that are fully or nearly complementary or identical to a plurality of miRNA molecules or precursor miRNA molecules and that are positioned on a support material in a spatially separated organization. Macroarrays are typically sheets of nitrocellulose or nylon upon which probes have been spotted. Microarrays position the nucleic acid probes more densely such that up to 10,000 nucleic acid molecules can be fit into a region typically 1 to 4 square centimeters. Microarrays can be fabricated by spotting nucleic acid molecules, e.g., genes, oligonucleotides, etc., onto substrates or fabricating oligonucleotide sequences in situ on a substrate. Spotted or fabricated nucleic acid molecules can be applied in a high density matrix pattern of up to about 30 non-identical nucleic acid molecules per square centimeter or higher, e.g. up to about 100 or even 1000 per square centimeter. Microarrays typically use coated glass as the solid support, in contrast to the nitrocellulose-based material of filter arrays. By having an ordered array of miRNA-complementing nucleic acid samples, the position of each sample can be tracked and linked to the original sample. A variety of different array devices in which a plurality of distinct nucleic acid probes are stably associated with the surface of a solid support are known to those of skill in the art. Useful substrates for arrays include nylon, glass and silicon. The arrays may vary in a number of different ways, including average probe length, sequence or types of probes, nature of bond between the probe and the array surface, e.g. covalent or non-covalent, and the like. The labeling and screening methods described herein and the arrays are not limited in its utility with respect to any parameter except that the probes detect miRNA; consequently, methods and compositions may be used with a variety of different types of miRNA arrays. In certain embodiments, the miR gene product comprises one or more of the SEQ ID NOS: 1-22, as shown in FIG. 11. In particular certain embodiments, one miR gene product comprises one or more of: miR-219 [SEQ ID NO: 20], miR-207 [SEQ ID NO: 18], miR-30c [SEQ ID NO: 6], and miR124A [SEQ ID NO: 4].

In accordance with the provisions of the patent statutes, the principle and mode of operation of this invention have been explained and illustrated in its preferred embodiment. However, it must be understood that this invention may be practiced otherwise than as specifically explained and illustrated without departing from its spirit or scope.

REFERENCES

The references discussed above and the following references, to the extent that they provide exemplary procedural or other details supplementary to those set forth herein, are specifically incorporated herein by reference.

References for Example I (1) Thorgeirsson S S, Grisham J W. Molecular pathogenesis of human hepatocellular carcinoma. Nat Genet 2002; 31(4):339-346.
(2) Parkin D M, Bray F, Ferlay J, Pisani P. Global cancer statistics, 2002. CA Cancer J Clin 2005; 55(2):74-108.
(3) Yuki K, Hirohashi S, Sakamoto M, Kanai T, Shimosato Y. Growth and spread of hepatocellular carcinoma. A review of 240 consecutive autopsy cases. Cancer 1990; 66(10): 2174-2179.
(4) Chambers A F, Groom A C, MacDonald I C. Dissemination and growth of cancer cells in metastatic sites. Nat Rev Cancer 2002; 2(8):563-572.
(5) Tang Z Y. Hepatocellular carcinoma-Cause, treatment and metastasis. World J Gastroenterol 2001; 7(4):445-454.
(6) Nakakura E K, Choti M A. Management of hepatocellular carcinoma. Oncology (Huntingt) 2000; 14(7):1085-1098.
(7) Wildi S, Pestalozzi B C, McCormack L, Clavien P A. Critical evaluation of the different staging systems for hepatocellular carcinoma. Br J Surg 2004; 91(4):400-408.
(8) Okuda K, Ohtsuki T, Obata H et al. Natural history of hepatocellular carcinoma and prognosis in relation to treatment. Study of 850 patients. Cancer 1985; 56(4):918-928.
(9) Levy I, Sherman M. Staging of hepatocellular carcinoma: assessment of the CLIP, Okuda, and Child-Pugh staging systems in a cohort of 257 patients in Toronto. Gut 2002; 50(6):881-885.
(10) Farinati F, Rinaldi M, Gianni S, Naccarato R. How should patients with hepatocellular carcinoma be staged? Validation of a new prognostic system. Cancer 2000; 89(11):2266-2273.
(11) Kudo M, Chung H, Osaki Y. Prognostic staging system for hepatocellular carcinoma (CLIP score): its value and limitations, and a proposal for a new staging system, the Japan Integrated Staging Score (MS score). J Gastroenterol 2003; 38(3):207-215.
(12) Cillo U, Bassanello M, Vitale A et al. The critical issue of hepatocellular carcinoma prognostic classification: which is the best tool available? J Hepatol 2004; 40(1):124-131.
(13) Ye Q H, Qin L X, Forgues M et al. Predicting hepatitis B virus-positive metastatic hepatocellular carcinomas using gene expression profiling and supervised machine learning. Nat Med 2003; 9(4):416-423.
(14) Iizuka N, Oka M, Yamada-Okabe H et al. Oligonucleotide microarray for prediction of early intrahepatic recurrence of hepatocellular carcinoma after curative resection. Lancet 2003; 361(9361):923-929.
(15) Lee J S, Chu I S, Heo J et al. Classification and prediction of survival in hepatocellular carcinoma by gene expression profiling. Hepatology 2004; 40(3):667-676.
(16) Budhu A, Forgues M, Ye Q H et al. Prediction of venous metastases, recurrence and prognosis in hepatocellular carcinoma based on a unique immune response signature of the liver microenvironment. Cancer Cell 2006; 10(2):99-111.
(17) Calin G A, Ferracin M, Cimmino A et al. A MicroRNA signature associated with prognosis and progression in chronic lymphocytic leukemia. N Engl J Med 2005; 353 (17):1793-1801.
(18) Calin G A, Liu C G, Sevignani C et al. MicroRNA profiling reveals distinct signatures in B cell chronic lymphocytic leukemias. Proc Natl Acad Sci USA 2004; 101 (32):11755-11760.
(19) Lu J, Getz G, Miska E A et al. MicroRNA expression profiles classify human cancers. Nature 2005; 435(7043): 834-838.
(20) Lee R C, Ambros V. An extensive class of small RNAs in *Caenorhabditis elegans*. Science 2001; 294(5543):862-864.
(21) Lau N C, Lim L P, Weinstein E G, Bartel D P. An abundant class of tiny RNAs with probable regulatory roles in *Caenorhabditis elegans*. Science 2001; 294(5543):858-862.
(22) Lagos-Quintana M, Rauhut R, Lendeckel W, Tuschl T. Identification of novel genes coding for small expressed RNAs. Science 2001; 294(5543):853-858.
(23) Yi R, Qin Y, Macara I G, Cullen B R. Exportin-5 mediates the nuclear export of pre-microRNAs and short hairpin RNAs. Genes Dev 2003; 17(24):3011-3016.
(24) Gregory R I, Shiekhattar R. MicroRNA biogenesis and cancer. Cancer Res 2005; 65(9):3509-3512.
(25) Lee Y, Jeon K, Lee J T, Kim S, Kim V N. MicroRNA maturation: stepwise processing and subcellular localization. EMBO J 2002; 21(17):4663-4670.
(26) Hutvagner G, Zamore P D. A microRNA in a multiple-turnover RNAi enzyme complex. Science 2002; 297 (5589):2056-2060.
(27) Metzler M, Wilda M, Busch K, Viehmann S, Borkhardt A. High expression of precursor microRNA-155BIC RNA in children with Burkitt lymphoma. Genes Chromosomes Cancer 2004; 39(2):167-169.
(28) Takamizawa J, Konishi H, Yanagisawa K et al. Reduced expression of the let-7 microRNAs in human lung cancers in association with shortened postoperative survival. Cancer Res 2004; 64(11):3753-3756.
(29) Michael M Z, O'Connor S M, Holst Pellekaan N G, Young G P, James Reduced accumulation of specific microRNAs in colorectal neoplasia. Mol Cancer Res 2003; 1(12):882-891.
(30) Iorio M V, Ferracin M, Liu C G et al. MicroRNA gene expression deregulation in human breast cancer. Cancer Res 2005; 65(16):7065-7070.
(31) Calin G A, Dumitru C D, Shimizu M et al. Frequent deletions and down-regulation of micro-RNA genes miR15 and miR16 at 13g14 in chronic lymphocytic leukemia. Proc Natl Acad Sci USA 2002; 99(24):15524-15529.
(32) Sonoki T, Iwanaga E, Mitsuya H, Asou N. Insertion of microRNA-125b-1, a human homologue of lin-4, into a rearranged immunoglobulin heavy chain gene locus in a patient with precursor B-cell acute lymphoblastic leukemia. Leukemia 2005; 19(11):2009-2010.
(33) Cimmino A, Calin G A, Fabbri M et al. miR-15 and miR-16 induce apoptosis by targeting BCL2. Proc Natl Acad Sci USA 2005.
(34) Chan J A, Krichevsky A M, Kosik K S. MicroRNA-21 is an antiapoptotic factor in human glioblastoma cells. Cancer Res 2005; 65(14):6029-6033.
(35) Johnson S M, Grosshans H, Shingara J et al. RAS is regulated by the let-7 microRNA family. Cell 2005; 120(5):635-647.
(36) Hayashita Y, Osada H, Tatematsu Y et al. A polycistronic microRNA cluster, miR-17-92, is overexpressed in human lung cancers and enhances cell proliferation. Cancer Res 2005; 65(21):9628-9632.
(37) Meng F, Henson R, Lang M et al. Involvement of human micro-RNA in growth and response to chemotherapy in human cholangiocarcinoma cell lines. Gastroenterology 2006; 130(7):2113-2129.
(38) Volinia S, Calin G A, Liu C G et al. A microRNA expression signature of human solid tumors defines cancer gene targets. Proc Natl Acad Sci USA 2006; 103(7):2257-2261.
(39) Ambros V. MicroRNA pathways in flies and worms: growth, death, fat, stress, and timing. Cell 2003; 113(6): 673-676.
(40) Yanaihara N, Caplen N, Bowman E et al. Unique microRNA molecular profiles in lung cancer diagnosis and prognosis. Cancer Cell 2006; 9(3):189-198.
(41) Lewis B P, Burge C B, Bartel D P. Conserved seed pairing, often flanked by adenosines, indicates that thousands of human genes are microRNA targets. Cell 2005; 120(1):15-20.

References for Example II (1) Varotti G, Ramacciato G, Ercolani G et al. Comparison between the fifth and sixth editions of the AJCC/UICC TNM staging systems for hepatocellular carcinoma: multicentric study on 393 cirrhotic resected patients. Eur J Surg Oncol 2005; 31(7):760-767.
(2) Huang Y H, Chen C H, Chang T T et al. Evaluation of predictive value of CLIP, Okuda, TNM and JIS staging systems for hepatocellular carcinoma patients undergoing surgery. J Gastroenterol Hepatol 2005; 20(5):765-771.
(3) Llovet J M, Bru C, Bruix J. Prognosis of hepatocellular carcinoma: the BCLC staging classification. Semin Liver Dis 1999; 19(3):329-338.
(4) The Cancer of the Liver Italian Program (CLIP) investigators. A new prognostic system for hepatocellular carcinoma: a retrospective study of 435 patients: the Cancer of the Liver Italian Program (CLIP) investigators. Hepatology 1998; 28(3):751-755.
(5) Okuda K, Ohtsuki T, Obata H et al. Natural history of hepatocellular carcinoma and prognosis in relation to treatment. Study of 850 patients. Cancer 1985; 56(4):918928.
(6) International Union Against Cancer (UICC). TNM Classification of Malignant Tumours, 6th Edition. Hoboken, N.J.: John Wiley & Sons, 2002.
(7) Ye Q H, Qin L X, Forgues M et al. Predicting hepatitis B virus-positive metastatic hepatocellular carcinomas using gene expression profiling and supervised machine learning. Nat Med 2003; 9(4):416-423.

What is claimed is:

1. A method of determining whether a human subject has a poor survival prognosis for hepatocellular carcinoma (HCC), comprising:
  measuring the level of a miR gene product signature in a test sample of hepatocellular carcinoma (HCC) tissue from the human subject,
  the miR gene product signature consisting of miR gene products: miR-30c, mir-124a, miR-207 and miR-219; and
  determining the survival prognosis of the subject;
  wherein an alteration in the level of the miR gene product in the test sample, relative to the level of a corresponding level of miR gene product in a control sample of metastasis-free liver tissue, is indicative of the human subject having a poor survival prognosis for HCC;
  the alteration being wherein at least one of the levels of miR-219 and mir-207 are above the levels of the control level, and/or wherein the at least one of the levels of miR-30cand miR-124a are below the levels of the control sample.

2. A method of diagnosing whether a human subject has, or is at risk for developing, a HCC associated with a poor prognosis, comprising:
  (1) reverse transcribing RNA from a test sample of hepatocellular carcinoma (HCC) tissue obtained from the human subject to provide a set of target oligodeoxynucleotides;
  (2) hybridizing the target oligodeoxynucleotides to a microarray comprising miRNA-specific probe oligonucleotides to provide a hybridization profile for the test sample wherein the microarray comprises miRNA-specific probe oligonucleotides for a miR gene product signature consisting of miR gene products: miR-30c, mir-124a, miR-207 and miR-219;
  (3) comparing the test sample hybridization profile to a hybridization profile generated from a control sample of metastasis-free tissue,
  and, 4) diagnosing whether the human subject has or is at risk of developing a HCC associated with a poor prognosis based on an alteration in the miR gene product signature; the alteration being wherein at least one of the levels of miR-219 and mir-207 are above the levels of the control level, and/or wherein the at least one of the levels of miR-30c and miR-124a are below the levels of the control sample.

3. The method of claim 1, wherein the step of determining the survival prognosis of the subject distinguishes HCC venous metastasis from metastasis-free HCC.

4. The method of claim 1, wherein the step of determining the survival prognosis of the subject predicts survival and recurrence of HCC patients with multinodular or solitary tumors.

5. The method of claim 2, wherein the step (4) comprises distinguishing HCC venous metastasis from metastasis-free HCC.

6. The method of claim 2, wherein the step (4) comprises predicting survival and recurrence of HCC patients with multinodular or solitary tumors.

7. The method of claim 2, wherein a signature set of miR-219, miR-207, miR-30c and miR-124a hybridize to probes that are specific for miR-129, miR-207, miR-30c and miR-124a, respectively,
  and the presence of an increase in the level of miR-219 and miR-207, relative to the control sample, and a decrease in the level of miR-30c and miR-124a, relative to the control sample, is indicative of metastatic HCC in human patients, a prognosis of poor survival in human patients, or an increased risk for recurrence of HCC in human subjects having HCC.

8. A method for determining if a human subject having hepatocellular carcinoma (HCC) has an increased likelihood of having or developing metastatic HCC comprising:

assaying a nucleic acid sample obtained from liver cells of the human subject to determine the expression level of miR-30c, miR-124a, miR-207 and miR-219 in the nucleic acid sample, and determining that the human subject has an increased likelihood of having or developing metastatic HCC, if there is an increase in the expression level of miR-219 and miR-207 and a decrease in the expression level of miR-30c and miR-124a in said nucleic acid sample, as compared to a control nucleic acid sample.

9. A method for determining if a human subject having hepatocellular carcinoma (HCC) has an increased likelihood of recurrence of HCC or a poor survival outcome comprising:

assaying a nucleic acid sample obtained from liver cells of the human subject to determine the expression level of miR-30c, miR124a, miR-207 and miR-219 in the nucleic acid sample, and determining that the human subject has an increased likelihood of recurrence of HCC or a poor survival outcome, if there is an increase in the expression level of miR-219 and miR-207 and a decrease in the expression level of miR-30c and miR-124a in said nucleic acid sample, as compared to a control nucleic acid sample.

* * * * *

UNITED STATES PATENT AND TRADEMARK OFFICE
CERTIFICATE OF CORRECTION

PATENT NO. : 8,252,538 B2  
APPLICATION NO. : 12/513219  
DATED : August 28, 2012  
INVENTOR(S) : Carlo M. Croce et al.

Page 1 of 1

It is certified that error appears in the above-identified patent and that said Letters Patent is hereby corrected as shown below:

Title Page item (73),

Please correct the typographical error of the Assignees from;

"The Ohio State University, Columbus, OH (US); The United States of America as represented by the Secretary of the Department of Health and Human Services National Institute of Health, Office of Technology Transfer, Washington, DC (US); Liver Cancer Institute and Zhongshan Hospital, Fudan University, Shangai (CN)"

to the

--The Ohio State University, Columbus, OH (US); The Government of the United States of America as represented by the Secretary of the Department of Health and Human Services National Institute of Health, Office of Technology Transfer, Rockville, Maryland (US); Liver Cancer Institute and Zhongshan Hospital, Fudan University, Shangai (CN)--.

Column 25, line 51, after "miR-30c" add a space.

Signed and Sealed this  
Sixth Day of November, 2012

David J. Kappos  
*Director of the United States Patent and Trademark Office*

SEQUENCE LISTING

```
<160> NUMBER OF SEQ ID NOS: 22

<210> SEQ ID NO 1
<211> LENGTH: 22
<212> TYPE: RNA
<213> ORGANISM: Homo sapiens

<400> SEQUENCE: 1
ucguaccgug aguaauaaug cg                                              22

<210> SEQ ID NO 2
<211> LENGTH: 22
<212> TYPE: RNA
<213> ORGANISM: Homo sapiens

<400> SEQUENCE: 2
uggaguguga caauggguguu ug                                             22

<210> SEQ ID NO 3
<211> LENGTH: 22
<212> TYPE: RNA
<213> ORGANISM: Homo sapiens
```

-continued

```
<400> SEQUENCE: 3
ucagugcauc acagaacuuu gu                                      22

<210> SEQ ID NO 4
<211> LENGTH: 20
<212> TYPE: RNA
<213> ORGANISM: Homo sapiens

<400> SEQUENCE: 4
uaaggcacgc ggugaaugcc                                         20

<210> SEQ ID NO 5
<211> LENGTH: 22
<212> TYPE: RNA
<213> ORGANISM: Homo sapiens

<400> SEQUENCE: 5
uguaacagca acuccaugug ga                                      22

<210> SEQ ID NO 6
<211> LENGTH: 23
<212> TYPE: RNA
<213> ORGANISM: Homo sapiens

<400> SEQUENCE: 6
uguaaacauc cuacacucuc agc                                     23

<210> SEQ ID NO 7
<211> LENGTH: 22
<212> TYPE: RNA
<213> ORGANISM: Homo sapiens

<400> SEQUENCE: 7
uguaaacauc cucgacugga ag                                      22

<210> SEQ ID NO 8
<211> LENGTH: 22
<212> TYPE: RNA
<213> ORGANISM: Homo sapiens

<400> SEQUENCE: 8
ucagugcacu acagaacuuu gu                                      22

<210> SEQ ID NO 9
<211> LENGTH: 22
<212> TYPE: RNA
<213> ORGANISM: Homo sapiens

<400> SEQUENCE: 9
uguaaacauc cuugacugga ag                                      22

<210> SEQ ID NO 10
<211> LENGTH: 22
<212> TYPE: RNA
<213> ORGANISM: Homo sapiens

<400> SEQUENCE: 10
uggcaguguc uuagcugguu gu                                      22

<210> SEQ ID NO 11
<211> LENGTH: 22
<212> TYPE: RNA
<213> ORGANISM: Homo sapiens
```

-continued

```
<400> SEQUENCE: 11
ugagguagua guuuguacag uu                                              22

<210> SEQ ID NO 12
<211> LENGTH: 22
<212> TYPE: RNA
<213> ORGANISM: Homo sapiens

<400> SEQUENCE: 12
ucccugagac ccuaacuugu ga                                              22

<210> SEQ ID NO 13
<211> LENGTH: 22
<212> TYPE: RNA
<213> ORGANISM: Homo sapiens

<400> SEQUENCE: 13
uggaauguaa agaaguaugu au                                              22

<210> SEQ ID NO 14
<211> LENGTH: 23
<212> TYPE: RNA
<213> ORGANISM: Homo sapiens

<400> SEQUENCE: 14
ugugcaaauc uaugcaaaac uga                                             23

<210> SEQ ID NO 15
<211> LENGTH: 22
<212> TYPE: RNA
<213> ORGANISM: Homo sapiens

<400> SEQUENCE: 15
uagcagcaca uaaugguuug ug                                              22

<210> SEQ ID NO 16
<211> LENGTH: 23
<212> TYPE: RNA
<213> ORGANISM: Homo sapiens

<400> SEQUENCE: 16
ucuuugguua ucuagcugua uga                                             23

<210> SEQ ID NO 17
<211> LENGTH: 22
<212> TYPE: RNA
<213> ORGANISM: Homo sapiens

<400> SEQUENCE: 17
uggagagaaa ggcaguuccu ga                                              22

<210> SEQ ID NO 18
<211> LENGTH: 23
<212> TYPE: RNA
<213> ORGANISM: Homo sapiens

<400> SEQUENCE: 18 gcuucccug gcucuccucc cuc                                              23

<210> SEQ ID NO 19
<211> LENGTH: 21
<212> TYPE: RNA
<213> ORGANISM: Homo sapiens
```

```
<400> SEQUENCE: 19
ugauugucca aacgcaauuc u                                                      21

<210> SEQ ID NO 20
<211> LENGTH: 22
<212> TYPE: RNA
<213> ORGANISM: Homo sapiens

<400> SEQUENCE: 20
agaguugagu cuggacgucc cg                                                     22

<210> SEQ ID NO 21
<211> LENGTH: 22
<212> TYPE: RNA
<213> ORGANISM: Homo sapiens

<400> SEQUENCE: 21
aacaauaucc uggugcugag ug                                                     22

<210> SEQ ID NO 22
<211> LENGTH: 22
<212> TYPE: RNA
<213> ORGANISM: Homo sapiens

<400> SEQUENCE: 22
uccagcauca gugauuuugu ug                                                     22
```